(12) United States Patent
Wilson, Jr. et al.

(10) Patent No.: US 6,824,547 B2
(45) Date of Patent: Nov. 30, 2004

(54) ENDOSCOPIC CLIP APPLIER AND METHOD

(75) Inventors: Don Wilson, Jr., Raleigh, NC (US); Bryan D. Knodel, Flagstaff, AZ (US)

(73) Assignee: Pilling Weck Incorporated, Limerick, PA (US)

( * ) Notice: Subject to any disclaimer, the term of this patent is extended or adjusted under 35 U.S.C. 154(b) by 0 days.

(21) Appl. No.: 09/905,679

(22) Filed: Jul. 13, 2001

(65) Prior Publication Data

US 2003/0014060 A1 Jan. 16, 2003

(51) Int. Cl.⁷ .............................................. A61B 17/04
(52) U.S. Cl. ..................................................... 606/143
(58) Field of Search ................................ 606/142, 143

(56) References Cited

U.S. PATENT DOCUMENTS

| | | | | |
|---|---|---|---|---|
| 4,509,518 A | * | 4/1985 | McGarry et al. ........... | 606/143 |
| 4,662,373 A | * | 5/1987 | Montgomery et al. ...... | 606/143 |
| 4,834,096 A | | 5/1989 | Oh et al. | |
| 5,100,420 A | | 3/1992 | Green et al. | |
| 5,156,609 A | | 10/1992 | Nakao et al. | |
| 5,171,249 A | | 12/1992 | Stefanchik et al. | |
| 5,207,691 A | * | 5/1993 | Nardella ...................... | 606/142 |
| 5,403,327 A | | 4/1995 | Thornton et al. | |
| 5,573,541 A | * | 11/1996 | Green et al. ................. | 606/143 |
| 5,607,436 A | * | 3/1997 | Pratt et al. ................... | 606/143 |
| 5,626,585 A | | 5/1997 | Mittelstadt et al. | |
| RE35,525 E | | 6/1997 | Stefanchik et al. | |
| 5,645,551 A | | 7/1997 | Green et al. | |
| 5,700,271 A | | 12/1997 | Whitfield et al. | |
| 5,772,673 A | * | 6/1998 | Cuny et al. .................. | 606/142 |
| 5,938,667 A | * | 8/1999 | Peyser et al. ................ | 606/142 |
| 2002/0198549 A1 | * | 12/2002 | Sixto et al. .................. | 606/157 |

FOREIGN PATENT DOCUMENTS

| EP | 0 409 569 A1 | 1/1991 |
|---|---|---|
| EP | 0 510 826 A1 | 10/1992 |
| EP | 0 596 429 A1 | 5/1994 |

* cited by examiner

Primary Examiner—Gary Jackson
(74) Attorney, Agent, or Firm—Jenkins, Wilson & Taylor, P.A.

(57) ABSTRACT

An endoscopic clip applier is adapted to retain a plurality of polymeric latching clips in an elongate assembly, and includes a jaw assembly for applying a polymeric latching clip. The jaw assembly extends from the distal end of the elongate assembly. A clip feeding member is moveable between a proximal position and a distal position to advance clips in the clip applier and to feed a clip from the distal end of the elongate assembly to the jaw assembly. Additionally, a jaw actuating member is moveable between a proximal position and a distal position, and includes cam surfaces for closing the jaw assembly. The actuator assembly actuates the clip feeding member to advance clips in the clip-containing elongate assembly and into the jaw assembly and subsequently advances the jaw actuating member to close the jaw assembly.

9 Claims, 27 Drawing Sheets

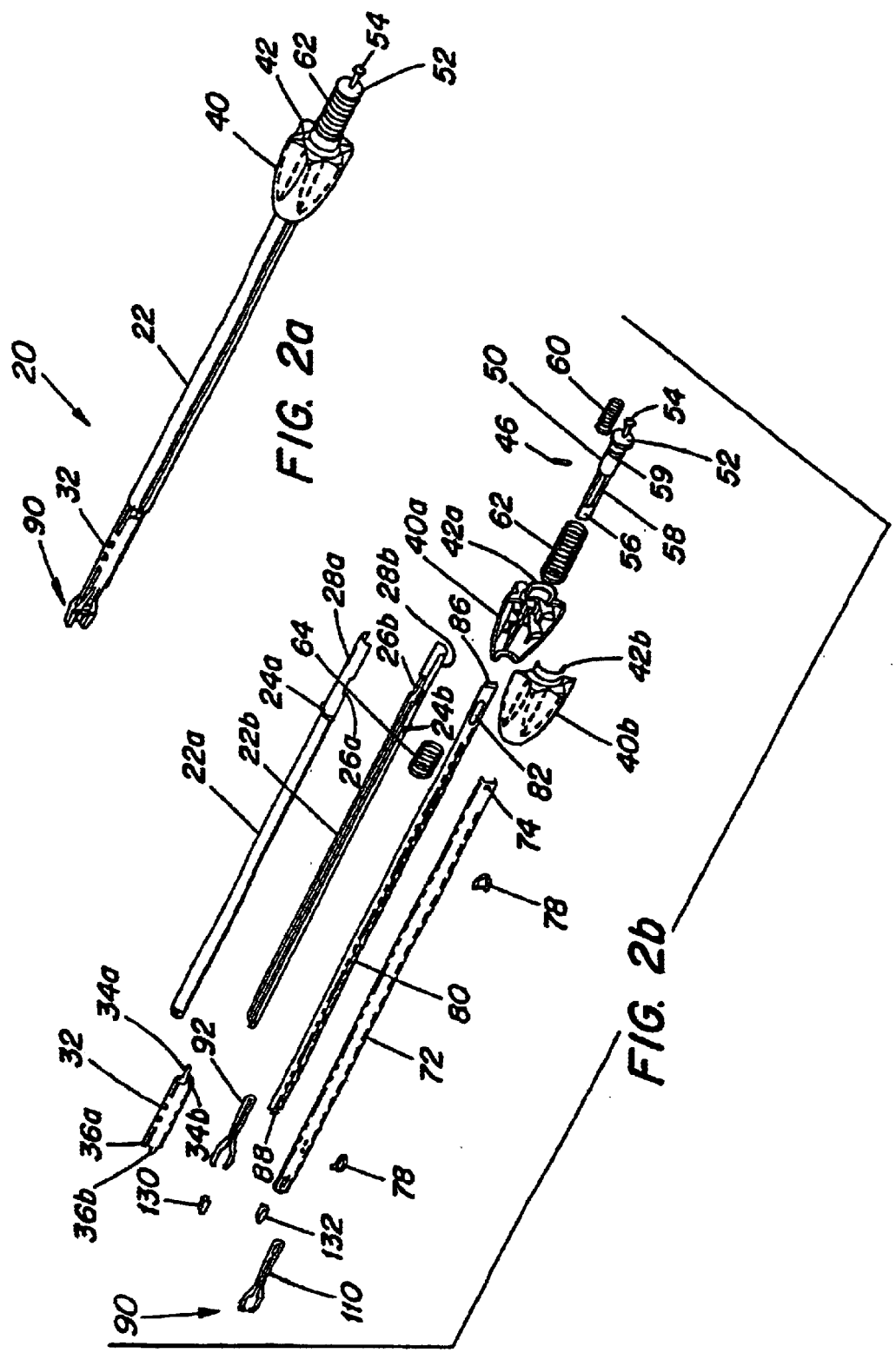

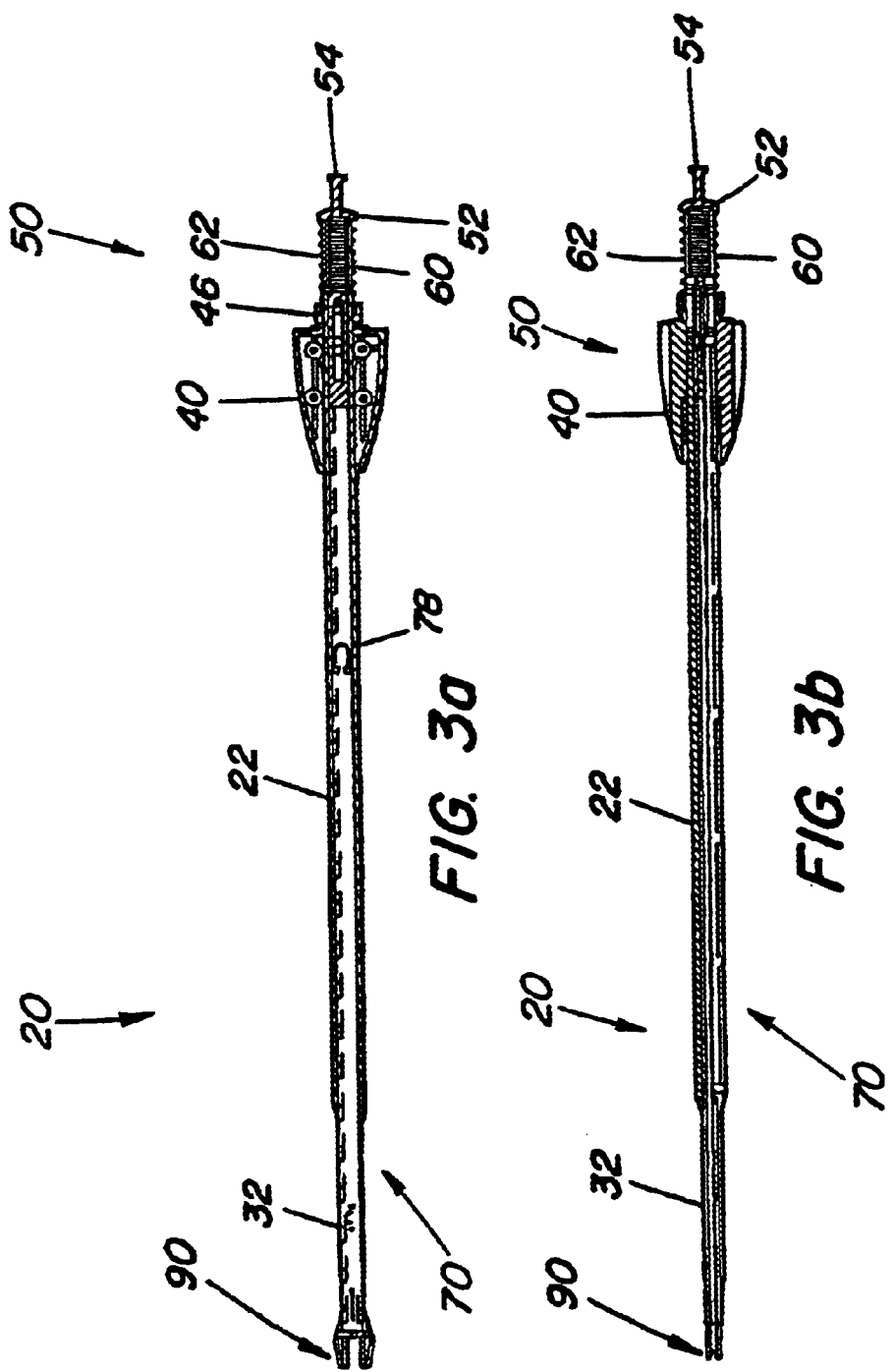

ENDOSCOPIC CLIP APPLIER AND METHOD

TECHNICAL FIELD

The subject matter disclosed herein generally relates to an applier for surgical clips. More particularly, the subject matter disclosed herein relates to a ligating clip applier capable of sequentially delivering a number of clips stored in a clip channel.

BACKGROUND ART

Laparoscopic, endoscopic, and other minimally invasive surgical techniques enable surgeons to perform fairly complicated procedures through relatively small entry points in the body. The term "laparoscopic" refers to surgical procedures performed on the interior of the abdomen, while the term "endoscopic" refers more generally to procedures performed in any portion of the body. Endoscopic surgery involves the use of an endoscope, which is an instrument permitting the visual inspection and magnification of a body cavity. The endoscope is inserted into a body cavity through a cannula extending through a hole in the soft tissue protecting the body cavity. The hole is made with a trocar, which includes a cutting instrument slidably and removably disposed within a trocar cannula. After forming the hole, the cutting instrument can be withdrawn from the trocar cannula. A surgeon can then perform diagnostic and/or therapeutic procedures at the surgical site with the aid of specialized medical instruments adapted to fit through the trocar cannula and additional trocar cannulas providing openings into the desired body cavity.

Some known advantages of minimally invasive surgical techniques include reduced trauma to the patient, reduced likelihood of infection at the surgical site, and lower overall medical costs. Accordingly, minimally invasive surgical techniques are being applied to an increasingly wider array of medical procedures.

Many surgical procedures require body vessels to be ligated during the surgical process. For example, many surgical procedures require cutting blood vessels (e.g., veins or arteries), and these blood vessels may require ligation to reduce bleeding. In some instances a surgeon may wish to ligate the vessel temporarily to reduce blood flow to the surgical site during the surgical procedure. In other instances a surgeon may wish to permanently ligate a vessel.

Vessel ligation may be performed by closing the vessel with a ligating clip, or by suturing the vessel with surgical thread. Performing vessel ligation using surgical thread requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. Accordingly, the use of ligating clips in endoscopic surgical procedures has grown dramatically.

Ligating clips may be classified according to their geometric configuration as either symmetric clips or asymmetric clips, and according to the material from which they are manufactured. Symmetric clips are generally "U" or "V" shaped metallic clips that are substantially symmetrical about a central, longitudinal axis extending between the legs of the clip. By contrast, asymmetric clips lack an axis of symmetry. For example, U.S. Pat. No. 4,834,096 to Oh et al. describes a polymeric, asymmetric surgical clip in which a first leg member includes a lip that mates with the second leg member to lock the clip in place. Asymmetric clips have certain advantages over symmetric clips. For example, because asymmetric clips are formed from polymeric materials, the mouths of asymmetric clips can be opened wider than the mouths of symmetric clips. This allows a surgeon to position the clip about the desired vessel with greater accuracy. In addition, a clip of the type described in U.S. Pat. No. 4,834,096 can be repositioned before locking or latching the clip on the vessel, a process referred to as "approximating" the clip, or to be removed from the vessel.

Ligating clips are applied using mechanical devices commonly referred to as surgical clip appliers, ligating clip appliers, or hemostatic clip appliers. Surgical clip appliers adapted for endoscopic surgical techniques include a shaft adapted to be inserted through an endoscopic cannula to access a surgical site in a body cavity and a jaw assembly disposed at the distal end of the shaft for retaining a surgical clip. In use, the clip is positioned over the desired vessel and the jaw is actuated, typically using a mechanism disposed in the handle of the device, to close the clip about the vessel.

Multiple clip applier systems have been developed that enable surgeons to deliver multiple symmetric surgical clips to an endoscopic surgical site. In general, these systems provide a surgical clip channel within the shaft of the device and a mechanism for delivering the surgical clips through the shaft to the jaw assembly. For example, U.S. Pat. Nos. 5,100,420 and 5,645,551 to Green et al. describe a device for delivering and applying multiple surgical clips to an endoscopic surgical site. Similarly, U.S. Pat. No. Re 35,525 to Stefanchik et al. aims to provide an endoscopic multiple ligating clip applier with a venting system. U.S. Pat. No. 5,700,271 to Whitfield et al., European Published Patent Application No. 0 409 569 A 1, and European Patent No. 0 596 429 B1 propose other clip applier designs.

As endoscopic techniques have been developed, certain inadequacies in the available surgical equipment have become apparent. For example, the jaws of the applier, which are typically used to close a clip around a vessel, may exert unequal pressure on the clip, resulting in a "scissoring" effect and damage to the vessel. In other instances, the clip may not be properly oriented when it is placed within the jaws or may slip out of alignment during application. This may result in the loss or misapplication of the clip. In still other instances, the applier may jam or may simply fail to deploy a clip.

Further, existing multiple clip applier systems have been designed for symmetric clips and are not well suited to satisfy design issues unique to asymmetric clips. For example, symmetric clips can be retained in clip jaws by holding opposing surfaces of the clip's legs in opposing channels. By contrast, asymmetric clips cannot easily be retained in opposing channels because the clip's legs deform when the clip is closed. In addition, when symmetric clips are closed on a vessel, the opposing legs of the clip apply substantially even pressure to the opposing sides of the vessel. By contrast, the opposing legs of an asymmetric clip may apply varying pressure to opposing sides of a vessel when the asymmetric clip is closed. Further, locking or latching asymmetric clips of the type described in U.S. Pat. No. 4,834,096 function best when force is applied at or near the distal ends of the clip legs. Still further, asymmetric clips of the type described in U.S. Pat. No. 4,834,096 may need to be placed under compression to be retained in the clip channel. Thus, conventional clip advancing mechanisms designed for symmetric clips may not reliably advance asymmetric clips. In addition, conventional clip advancing mechanisms designed for symmetric clips may not provide the ability to approximate a clip.

In sum, conventional clip appliers designed for symmetric, metal clips suffer from certain deficiencies and are not adapted to deliver asymmetric, polymer based latching clips. Accordingly, there is a need to provide an endoscopic clip applier that can reliably deliver a sequence of clips and in a manner which minimizes the risk of damage to the vessel. Further there is a need for an endoscopic clip applier adapted to deliver asymmetric, polymer ligating clips.

SUMMARY

According to one embodiment, an apparatus is provided for applying polymeric latching clips in an endoscopic surgical procedure. The apparatus comprises an elongate assembly for containing polymeric latching clips, and a jaw assembly for receiving a clip from the elongate assembly. The elongate assembly comprises a distal end. The jaw assembly comprises first, second, third and fourth jaw legs spaced apart from each other for substantially simultaneously engaging at least four portions of the clip. Each leg extends from the distal end and is actuatable toward at least one other opposing leg for compressing the clip.

According to another embodiment, an apparatus is provided for applying polymeric latching clips in an endoscopic surgical procedure. The apparatus comprises an elongate assembly for containing polymeric latching clips, a jaw assembly, and an actuator assembly. The elongate assembly comprises an axially movable distal end section. The distal end section comprises a plurality of distal cam surfaces generally spaced around a cross-section of the distal end section. The jaw assembly comprises first and second opposing jaws for compressing a clip therebetween. The jaw assembly extends from the elongate assembly. The actuator assembly communicates with the distal end section for actuating the distal cam surfaces into contact with the jaw assembly to cam the first and second jaws toward each other.

According to yet another embodiment, an apparatus is provided for applying polymeric latching clips in an endoscopic surgical procedure. The apparatus comprises an elongate assembly for containing polymeric latching clips, a jaw assembly, and an actuator assembly. The elongate assembly comprises a distal end, an axially movable clip feeding member, and an axially movable jaw actuating member. The jaw assembly extends from the distal end and comprises first and second opposing jaws for compressing a clip therebetween. The actuator assembly is actuatable through a first stage and a subsequent second stage of a forward stroke. The actuator assembly is coupled with the clip feeding member for moving the clip feeding member into contact with the clip to feed the clip into the jaw assembly during the first stage. The actuator assembly communicates with the jaw actuating member for moving the jaw actuating member into contact with the jaw assembly to close the clip during the second stage. The clip feeding member remains coupled with the actuator assembly for maintaining contact with the clip during the second stage.

According to still another embodiment, an apparatus is provided for applying polymer latching clips in an endoscopic surgical procedure. The apparatus comprises an elongate assembly for containing polymeric latching clips, a jaw assembly, and an actuator assembly. The elongate assembly comprises a distal end and an axially movable clip feeding device. The jaw assembly extends from the distal end and comprises first and second opposing jaws for compressing a clip therebetween. The first and second jaws comprise respective first and second hook structures. The actuator assembly is coupled with the clip feeding device for moving the clip feeding device toward the jaw assembly during a clip feeding stroke and a subsequent clip opening stroke. During the clip feeding stroke, the actuator assembly moves the clip feeding device into contact with the clip for feeding the clip from the elongate assembly into the jaw assembly. During the clip opening stroke, the actuator assembly through the clip feeding device urges the clip against the first and second hook structures for forcing the clip and the first and second jaws into a fully open position.

According to a further embodiment, an apparatus is provided for applying polymeric latching clips in an endoscopic surgical procedure. The apparatus comprises an elongate assembly for containing polymeric latching clips, a jaw assembly, and a clip feeding member. The elongate assembly comprises an elongate assembly distal end. The jaw assembly extends from the elongate assembly distal end for receiving a clip from the elongate assembly. The clip feeding member is axially movable along a length of the elongate assembly for feeding the clip into the jaw assembly. The clip feeding member comprises a feeding member proximal end for coupling with an actuator, and an opposing feeding member distal end. The feeding member distal end comprises a feeder tab. The feeder tab comprises a concave surface for contacting a convex proximal hinge portion of the clip.

According to a yet further embodiment, an apparatus is provided for applying polymeric latching clips in an endoscopic surgical procedure. The apparatus comprises an elongate assembly for containing polymeric latching clips, a jaw assembly for receiving clips from the elongate assembly, an actuator assembly, and a ratchet member. The elongate assembly comprises a clip feeding member and a jaw actuating member. The actuator assembly comprises a ratchet surface. The actuator assembly is coupled to the clip feeding member for moving the clip feeding member in a distal direction during a first stroke portion for feeding a clip into the jaw assembly and forcing said clip to an open position once in the jaw assembly. The actuator assembly communicates with the jaw actuating member for moving the jaw actuating member into engagement with the jaw assembly during a second stroke portion for closing the jaw assembly and allowing the jaw assembly to reopen. The ratchet member is coupled to the actuator assembly. The ratchet member is actuatable into engagement with the ratchet surface during the first stroke portion for preventing movement of the clip feeding member in a proximal direction. The ratchet member is actuatable out of engagement with the ratchet surface during the second stroke portion for enabling movement of the jaw actuating member in both the distal and proximal directions.

According to an additional embodiment, an apparatus is provided for applying polymeric latching clips in an endoscopic surgical procedure. The apparatus comprises an elongate assembly for containing polymeric latching clips, a jaw assembly, a clip feeding member, an actuator assembly, and a clip rotating member. The elongate assembly comprises a distal end. The jaw assembly extends from the distal end for receiving clips from the elongate assembly. The clip feeding member is axially movable along a length of the elongate assembly for feeding a clip into the jaw assembly. The actuator assembly is actuatable through a forward stroke and a return stroke. The actuator assembly is coupled to the clip feeding member for moving the clip feeding member toward the jaw assembly during the forward stroke to feed a clip therein, and for moving the clip feeding member away from the jaw assembly during the return stroke. The clip rotating member is disposed in the distal end and is contactable with the clip for rotating the clip in response to movement of the clip feeding member.

According to a method for applying a polymeric latching clip at a surgical site, a clip disposed in a clip applying apparatus is fed into a jaw assembly thereof. The jaw assembly comprises at least four jaw legs substantially simultaneously engaging at least four respective portions of the clip. The jaw assembly is actuated to compress the clip while the at least four clip portions remain respectively engaged with the at least four jaw legs to stabilize the clip during compression.

According to another method for applying a polymeric latching clip at a surgical site, a clip disposed in a clip applying apparatus is fed into a jaw assembly thereof. The jaw assembly comprises first and second opposing jaws. The first and second jaws are cammed together to compress the clip. The camming is accomplished by moving at least first and second jaw actuating surfaces into contact with the first jaw, and moving at least third and fourth jaw actuating surfaces into contact with the second jaw. The clip is thereby compressed in a stable manner and is subjected to forces distributed among the at least first, second, third and fourth jaw actuating surfaces.

According to yet another method for applying a polymeric latching clip at a surgical site, a clip disposed in a clip applying apparatus is fed into a jaw assembly thereof. The jaw assembly is actuated to compress the clip by moving first and second opposing legs of the clip toward each other. A rear portion of the clip adjoining the first and second clip legs is engaged while actuating the jaw assembly to stabilize the clip during compression thereof.

According to a method for preparing a polymeric latching clip for application at a surgical site, a clip disposed in a clip applying apparatus is fed into first and second opposing jaws of a jaw assembly of the apparatus. The first jaw comprises a first hook structure, and the second jaw comprises a second hook structure. Feeding the clip causes the first and second opposing legs of the clip to engage the first and second hook structures, respectively. The first and second clip legs are urged against the respective first and second hook structures to urge the clip and the jaw assembly into a fully open state for facilitating positioning the clip at a surgical site in preparation for applying the clip.

According to a method for enabling a polymeric latching clip to be approximated in preparation for applying the clip at a surgical site, a clip feeding device of a clip applying apparatus is actuated in a distal direction to feed a clip into a jaw assembly of the apparatus during a first stage of a forward stroke of the apparatus. The clip is prevented from moving in a proximal direction away from the jaw assembly during the first stage. During a second stage of the forward stroke subsequent to the first stage, the jaw assembly is enabled to be selectively actuated between alternate open and closed positions for controllably manipulating the clip during the second stage in preparation for applying the clip.

According to another method for preparing a polymeric latching clip for application at a surgical site, a clip disposed in a clip applying apparatus is rotated to align a rear portion of the clip adjoining two opposing legs thereof with a feeder tab of the apparatus. The clip is fed into a jaw assembly of the apparatus by actuating the feeder tab into contact with the rear clip portion.

It is therefore an object of the subject matter disclosed herein to provide an endoscopic clip applier and method.

BRIEF DESCRIPTION OF DRAWINGS

Objects and advantages of the subject matter disclosed herein will be understood by reading the following detailed description in conjunction with the drawings in which:

FIG. 2a is a perspective view of a shaft assembly of a clip applier in accordance with the subject matter disclosed herein;

FIG. 2b is an assembly view of the shaft assembly depicted in FIG. 2a;

FIG. 3a is a cross-sectional view, taken in a plane parallel to the jaw members, of a shaft assembly of a clip applier in accordance with the subject matter disclosed herein;

FIG. 3b is a cross-sectional view, taken in a plane perpendicular to the jaw members, of a shaft assembly of a clip applier in accordance with the subject matter disclosed herein;

DETAILED DESCRIPTION

Figure 1:
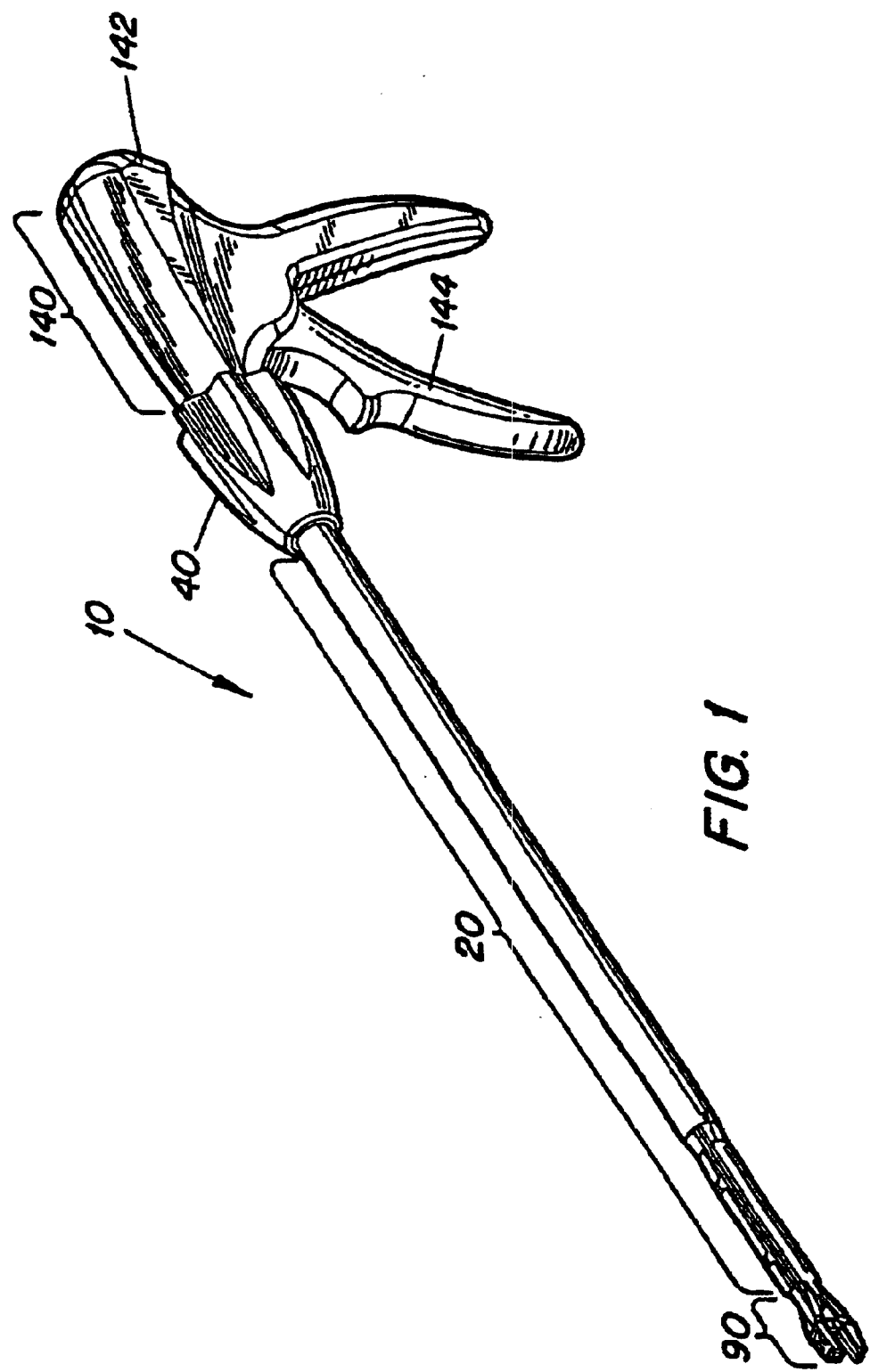
FIG. 1 is a perspective view of a clip applier constructed in accordance with the subject matter disclosed herein.

Referring to FIG. 1, an exemplary embodiment of an endoscopic clip applier 10 in accordance with the subject matter disclosed herein includes an elongate or shaft assembly, generally designated 20, a jaw assembly generally designated 90 disposed at a distal end thereof, and a handle assembly generally designated 140 disposed at a proximal end thereof. The handle assembly 140 includes a stationary grip 142 and a moveable trigger 144 for actuating the clip applier 10. In use, the jaw assembly 90 may be positioned inside a body cavity, for example by passing the shaft assembly 20 through an endoscopic cannula, to apply a ligating clip to a body vessel.

Figure 2C:
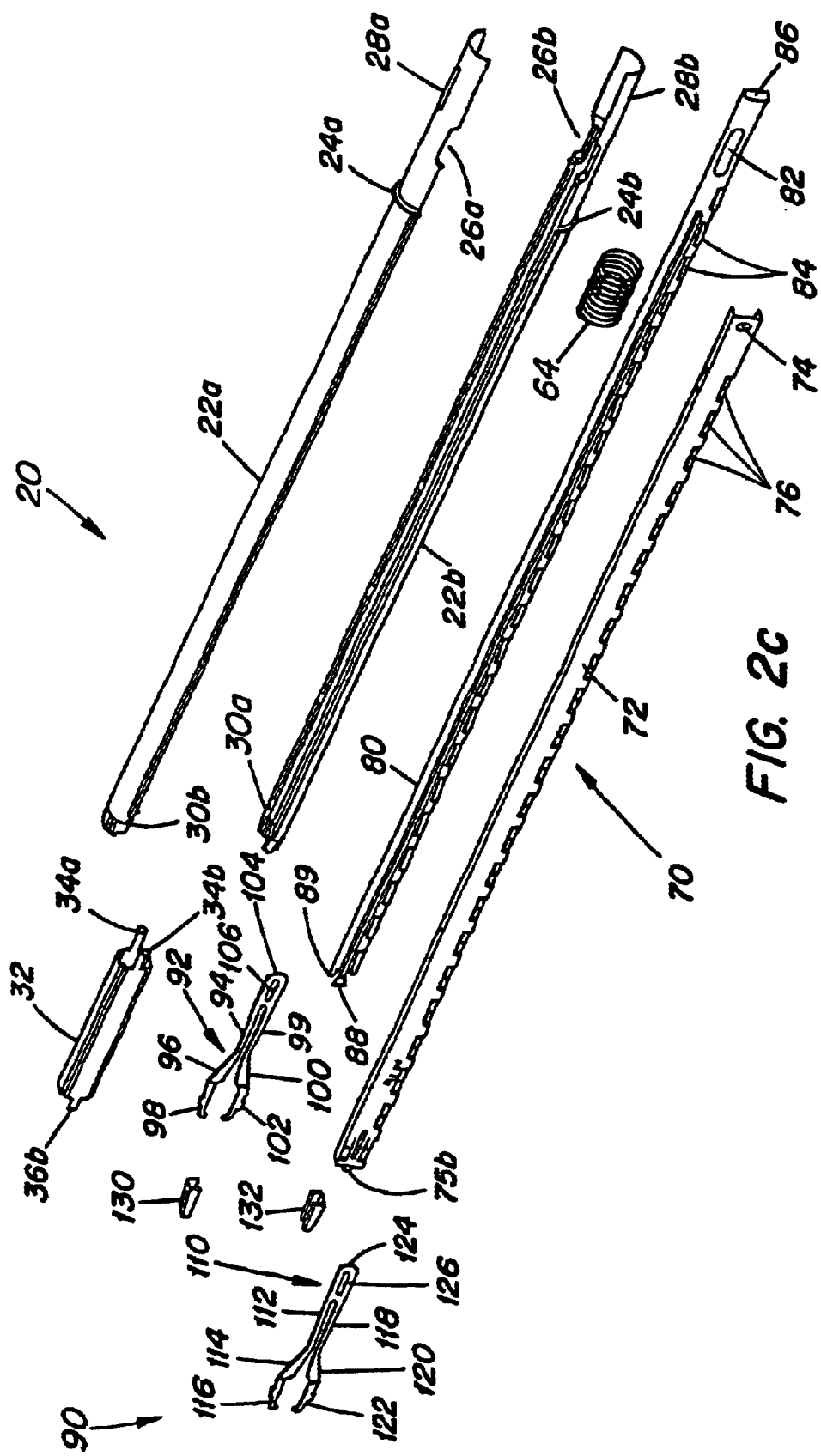
FIG. 2c is an enlarged assembly view of portions of the shaft assembly depicted in FIG. 2b.

FIG. 2a is a perspective view and FIGS. 2b and 2c are exploded assembly views of an exemplary embodiment of shaft assembly 20 and jaw assembly 90. Shaft assembly 20 includes an elongate member such as a cylindrical outer shaft member 22, which may be formed from two semi-cylindrical outer shaft members 22a and 22b, respectively. It will be appreciated that outer shaft member 22 may be formed from a single tubular member, or may be of a rectangular or polygonal cross-section. Outer shaft member 22 includes a proximal flange, indicated by proximal flange half sections 24a, 24b extending from the cylindrical surface of shaft members 22a and 22, respectively. Outer shaft member 22 further includes pin slots 28a, 28b formed in the cylindrical surface. In addition, the cylindrical surface of outer shaft members 22a, 22b include opposing channels 26a, 26b that define opposing slots when shaft member 22 is assembled. Outer shaft 22 may be formed from a suitably rigid material, e.g., a suitable polymer or metal.

Figure 18:
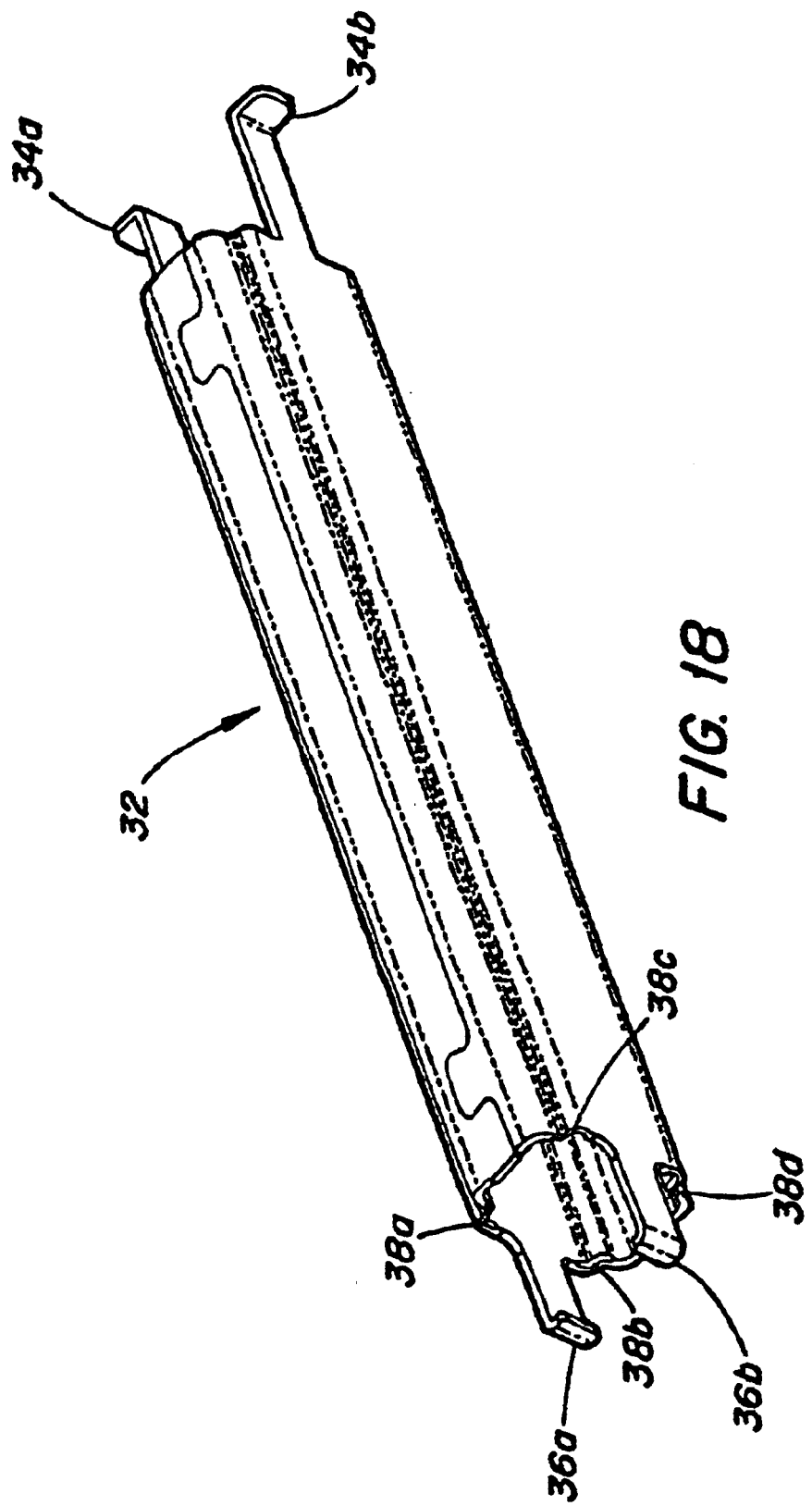
FIG. 18 is a perspective view of a collar in accordance with an embodiment of the subject matter disclosed herein.

With further reference to FIGS. 2a–2c, at the distal end, shaft 22 may taper from a cylindrical cross-section to a substantially rectangular cross-section. As best shown in FIG. 2d, shaft assembly 20 can include a collar 32 serving as a distal end section or interface between the main portion of outer shaft 22 and jaw assembly 90. Collar 32 has keys 34a, 34b that interlock with key slots 30a, 30b for connecting the collar 32 to outer shaft member 22. As best shown in FIG. 18, collar 32 preferably is substantially rectangular in cross-section and includes four cam surfaces 38a, 38b, 38c, 38d and opposing keys 36a, 36b at its distal end. Collar 32 may be formed from suitably rigid material, e.g., a suitable polymer or metal.

Referring to FIG. 2c, a clip feed assembly 70 is disposed within the shaft 22 and collar 32. Clip feed assembly 70 includes a channel 72 for housing clips 78 (FIG. 2b), and feeder bar 80 that is moveable along the longitudinal axis of shaft 22 for moving clips disposed in channel 72 toward the distal end of the applier 10. Channel 72 includes a pin hole 74 near the proximal end and a plurality of tabs 76 near its base. Channel 72 may be formed from suitably rigid material, e.g., a suitable polymer or metal.

Feeder bar 80 includes a pin slot 82 and a plurality of tabs 84 which act as clip advancing elements to move the clips 78 in channel 72 toward the distal end of the applier 10. Each tab 84 may be formed by stamping or cutting a portion of the body of the feeder bar 80. The tab 84 remains attached to the body of the feeder bar 80 at the proximal end of the tab 84. Each tab 84 may be bent or otherwise directed toward the interior of the clip channel 72. The tabs 84 may have a substantially uniform length, which may be determined by the length and geometry of the endoscopic clip, and by the rigidity of the material from which the feeder bar 80 is manufactured. The tabs 84 may be located along either the top or bottom (or both) edges of the side of the clip channel. Feeder bar 80 may be formed from suitably rigid material, e.g., a suitable polymer or metal.

As shown in FIG. 2b, shaft assembly 20 further includes a yoke, generally designated 50, a portion of which is disposed within the handle assembly 140 (FIG. 1), for translating longitudinal motion to feeder bar 80 and outer shaft 22. Feeder bar 80 includes a tab 86 that rests adjacent an interior distal edge 57 of yoke 50 (see also FIG. 15c). A portion of the yoke body 56 extends along a portion of the length of feeder bar 80 and has a slot 58 that aligns with pin slot 82 when yoke 50 is connected to feeder bar 80. Yoke 50 further includes a flange 52 and pin 54 on its proximal end. Yoke 50 may be formed from suitably rigid material, e.g., a suitable polymer or metal. A feeder spring 60 is positioned within the body 56 of yoke 50 for biasing the feeder bar 80 toward the distal end of yoke 50. A tube spring 62 is positioned between flange 52 and a flange (shown as flange halves 42a and 42b) on knob 40 for biasing the yoke 50 toward the proximal end of the shaft assembly 20. A knob spring 64 is disposed within knob 40 and biases the outer shaft 22 in a proximal direction.

Referring to FIG. 2c, jaw assembly 90 is connected to the distal end of clip channel 72. Jaw assembly 90 includes a first jaw member 92 having a first leg 94 and a second leg 99 connected by a bridge member 104. First leg 94 includes a first cam surface 96 and a first jaw arm 98, and second leg 99 includes a second cam surface 100 and a second jaw arm 102. Bridge member 104 includes a slot 106 for receiving a conventional fastener (e.g., rivets, pins, screws, tabs, etc.) to connect first jaw member 92 to channel 72. Jaw assembly 90 further includes a second jaw member 110 having a third leg 112 and a fourth leg 118 connected by a bridge member 124. Third leg 112 includes a third cam surface 114 and a third jaw arm 116, and fourth leg 118 includes a fourth cam surface 120 and a fourth jaw arm 122. Bridge member 124 includes a slot 126 for receiving a conventional fastener (e.g., rivets, pins, screws, tabs, etc.) to connect second jaw member 110 to channel 72. Jaw assembly 90 further includes a first guide 130 adapted to clip over first jaw arm 98 and third jaw arm 116 and a second guide 132 adapted to clip over second jaw arm 102 and fourth jaw arm 122. Jaw assembly 90 may be formed from suitably rigid material, e.g., a suitable polymer or metal.

FIGS. 3a and 3b are cross-sectional views of an assembled shaft assembly 20 of a clip applier 10 in accordance with the subject matter disclosed herein. When assembled, the jaw assembly 90, clip feed assembly 70, and yoke 50 are connected as described herein and extend through outer shaft 22. Knob 40 is mounted to the exterior of shaft 22 and secured using conventional fasteners (e.g., pins, rivets, screws, adhesives, etc.). A pin 46 extending through knob 40 and through pin hole 74 (FIG. 2c) in channel 72 retains channel 72 in a fixed position with respect to knob 40. For clarity, FIG. 3a illustrates a clip channel 72 having a single clip 78, but it will be appreciated that the clip channel 72 may be filled with a plurality (e.g., 2–100) clips. The diameter of shaft 22 is determined by the diameter of the cannula through which the shaft 22 must pass to enter a body cavity. Many existing surgical procedures use a cannula having an inner diameter measuring approximately 10 millimeters. Accordingly, in one embodiment of the invention, the shaft 22 has an outer diameter slightly less than 10 millimeters. In an alternate embodiment, the shaft 22 may be dimensioned to fit within a cannula having a diameter of 5 millimeters. It will be appreciated, however, that the diameter of the shaft 22 is not critical to the invention; any other diameter may be used as desired.

Figure 4:
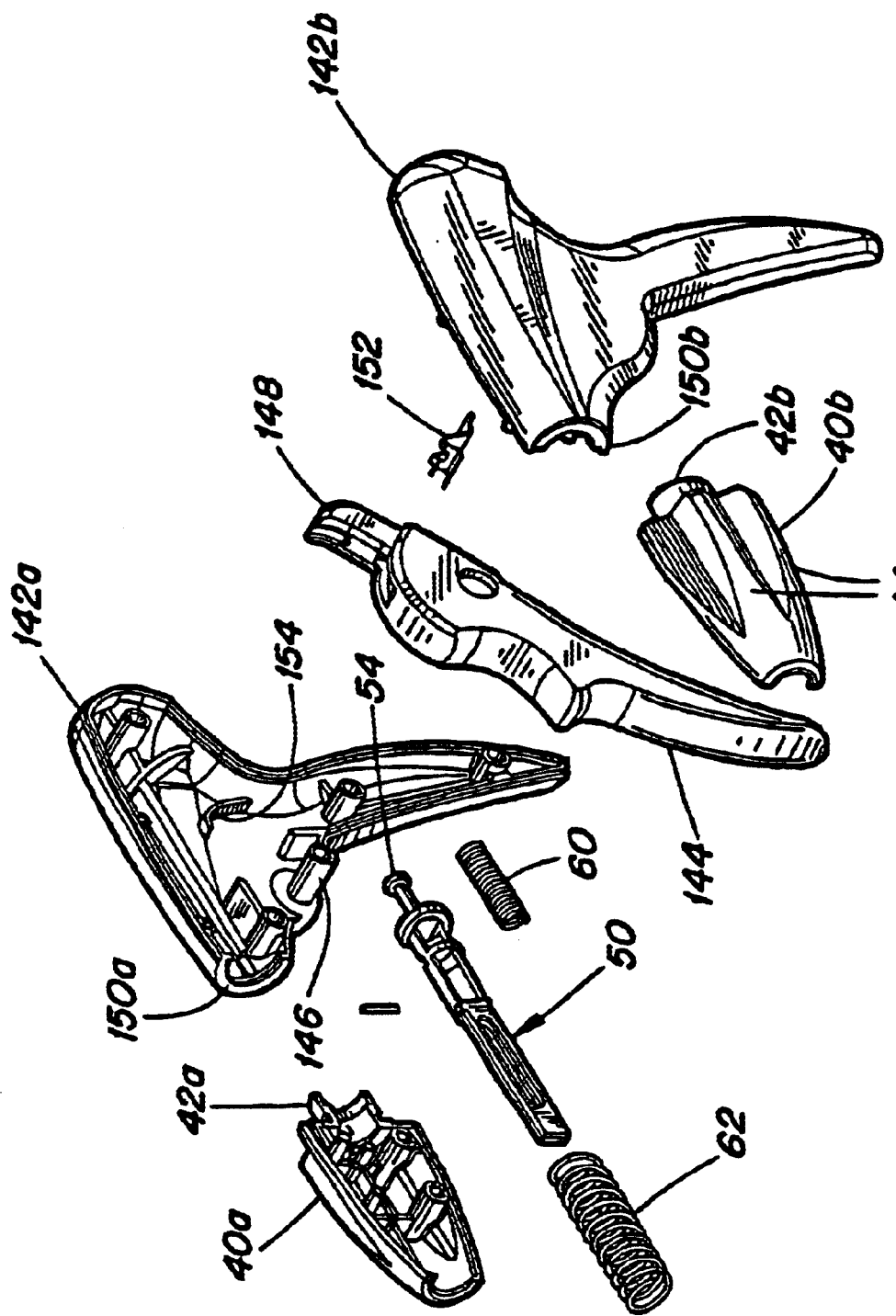
FIG. 4 is an assembly view of a handle assembly in accordance with the subject matter disclosed herein.
Figure 5:
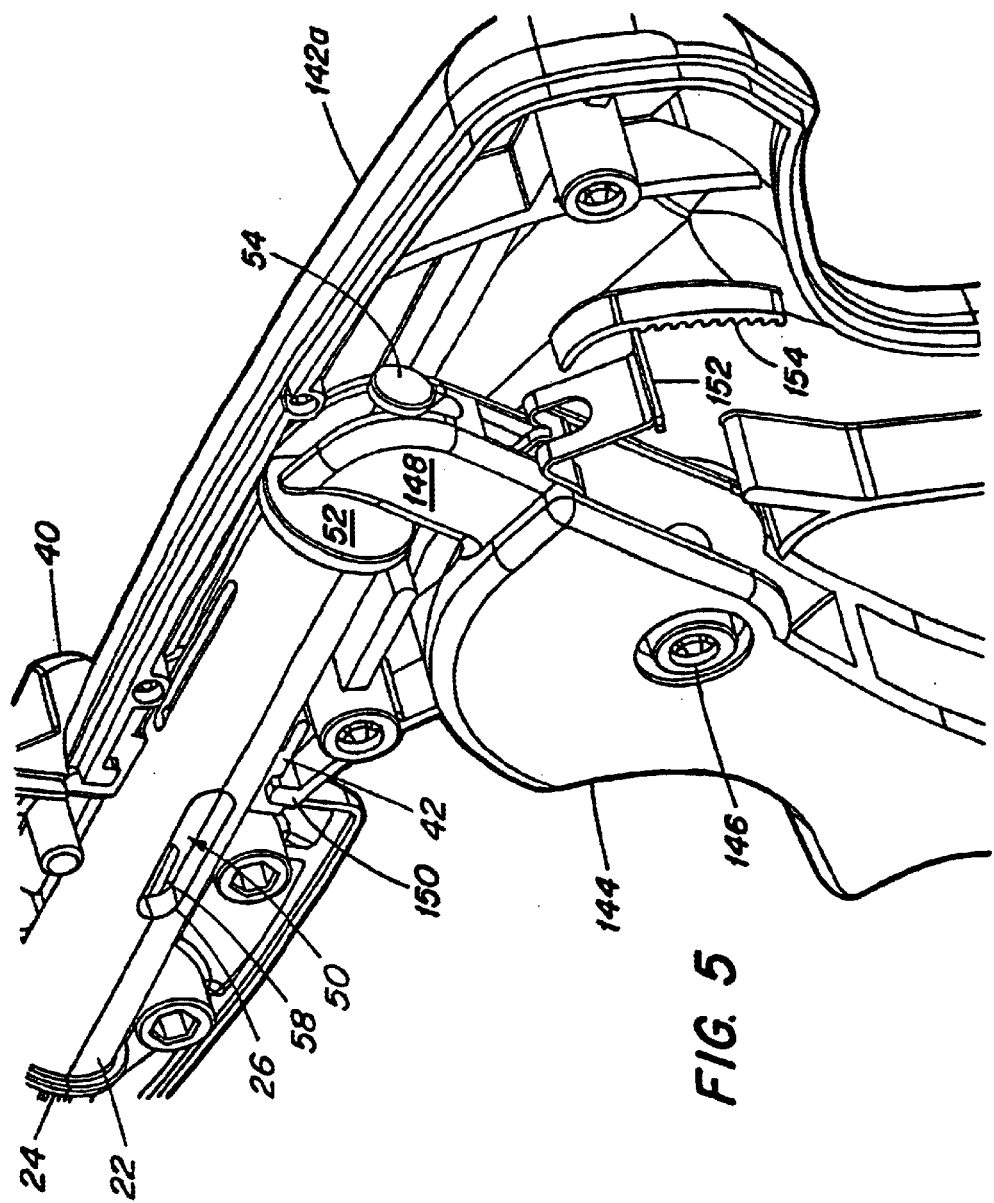
FIG. 5 is a perspective view of the interior of a handle assembly in accordance with the subject matter disclosed herein.

Referring to FIG. 4 and FIG. 5, a handle assembly 140 includes a fixed grip 142, which may be manufactured in two substantially symmetrical parts 142a, 142b. A trigger 144 is pivotally mounted to fixed grip 142 about a pivot point 146. As best shown in FIG. 5, trigger 144 includes a grooved claw 148 that impinges on flange 52 to translate the rotary motion of trigger 144 about pivot point 146 to linear motion of yoke 50 relative to fixed grip 142 in the distal direction. Grooved claw 148 also receives the pin 54 of yoke 50. This arrangement enables a user to force yoke 50 in a proximal direction if necessary, which provides a safety feature. Fixed grip 142 further includes a rim 150 that secures the flange 42 of knob 40, such that knob 40 and channel 72 are maintained in a substantially fixed longitudinal position relative to fixed grip 142. The entire shaft assembly 20 is rotatable about its longitudinal axis, and knob 40 includes fins 44 (FIG. 4) that facilitate rotating the shaft assembly 20.

A ratchet key 152 extends from the rear of trigger 144 and contacts ratchet guide 154 to inhibit backward motion of trigger 144 through a portion of the actuation stroke. Preferably, the toothed surface portion of ratchet guide 154 corresponds to the range of motion trigger claw 148 covers while the feeder bar 80 is moved forward to advance the clips in clip channel 72 (i.e., the feed stroke). The smooth surface portion of ratchet guide 154 preferably corresponds to the range of motion trigger claw 148 covers during the portion of the actuation stroke that closes the jaw assembly 90. When the device is actuated, the transition of the ratchet key 152 from the ratchet surface portion to the smooth surface portion provides the user with tactile feedback indicating that the feed stroke is complete and a clip 78 has been fed to the jaw assembly 90. In addition, the smooth surface portion permits a user to approximate a clip.

Basic structural elements of one embodiment of a clip applier 10 have been described with reference to FIGS. 1–5. The interaction of the structural elements and the operation of the device will be explained with reference to FIGS. 6–24.

Figure 6:
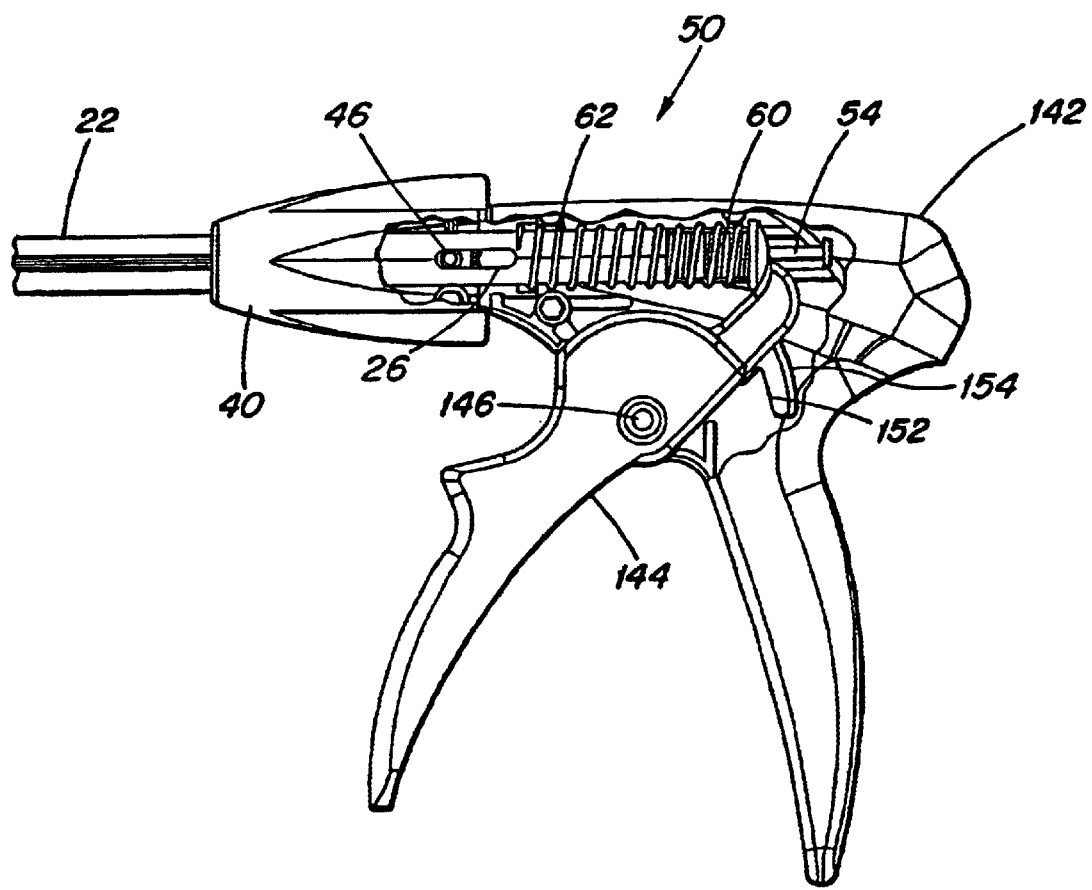
FIG. 6 is a partial cut-away view of a handle assembly in accordance with the subject matter disclosed herein.

FIG. 6 is a partial cut-away, side view of the proximal end of clip applier 10 with the device in an unactuated state. Referring to FIG. 6, yoke 50 is biased to its most proximal position by tube spring 62. In the unactuated state, jaw assembly 90 is partially open, as depicted in FIG. 1. Trigger 144 and yoke 50, in combination, may be considered an actuation assembly for actuating the clip feed assembly 70 and the jaw assembly 90.

Figure 7:
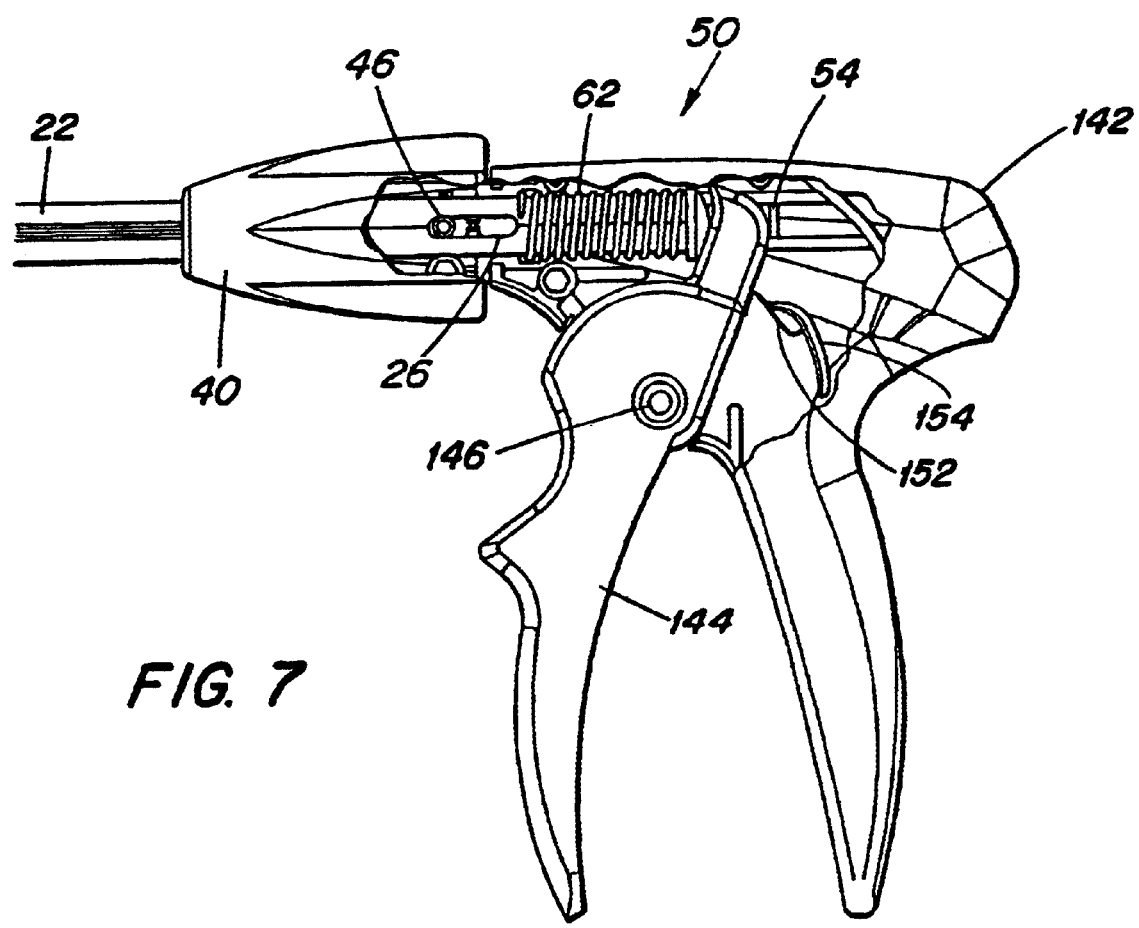
FIG. 7 is a partial cut-away view of a handle assembly in accordance with the subject matter disclosed herein.

FIG. 7 is a side cut-away view of the proximal end of clip applier 10 with the device in a partially actuated state. Forward motion of yoke 50 places tube spring 62 under compression. In one embodiment, the spring coefficient of feeder spring 60 (FIG. 6) is higher than the amount of force required to advance the feeder bar 80. Therefore, the feeder spring 60 effectively functions as a solid piece of material during the feed stroke.

Figure 8:
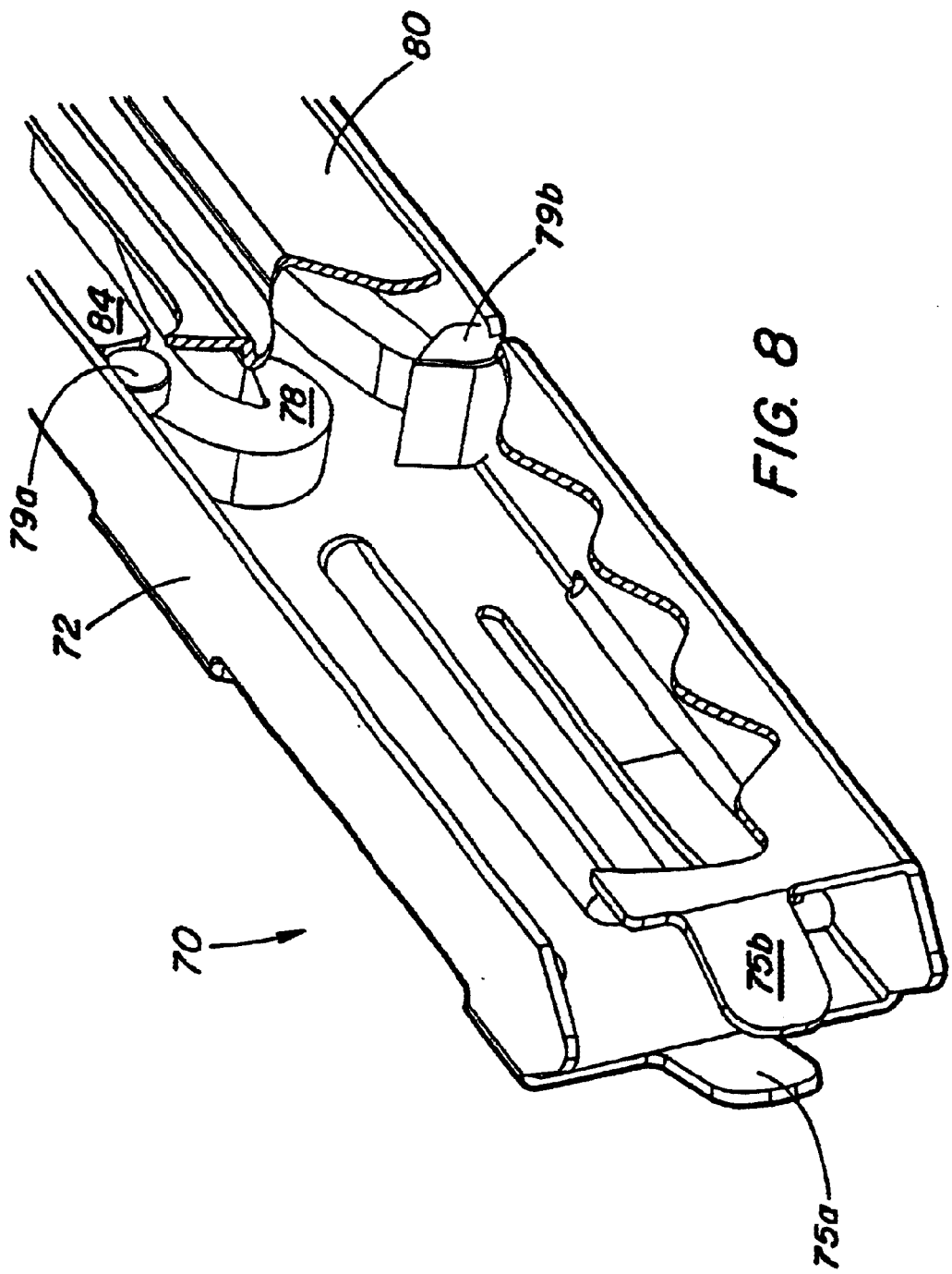
FIGS. 8–10 are partial cut-away views of a clip channel during a clip advancing process.
Figure 9:
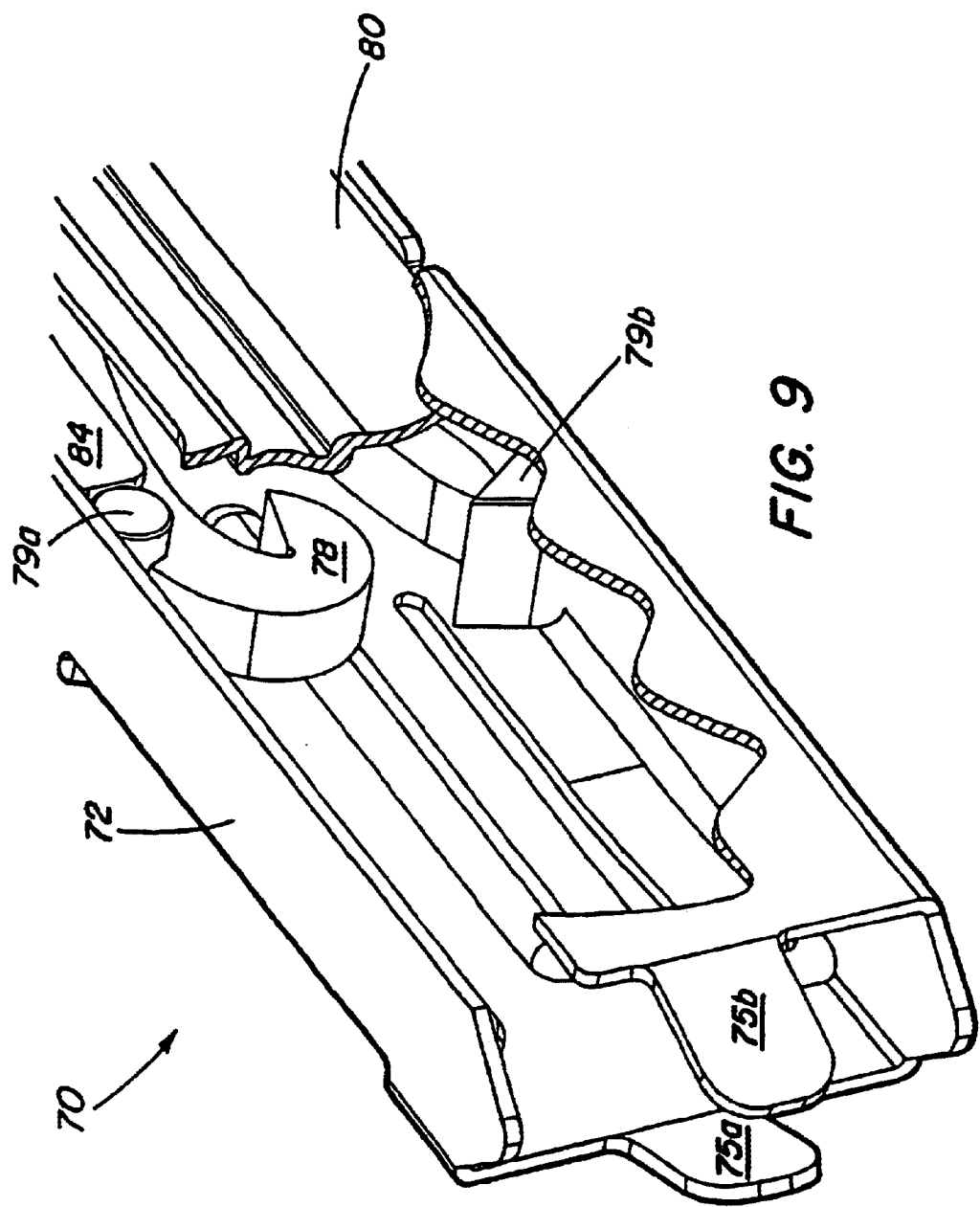
Figure 10:
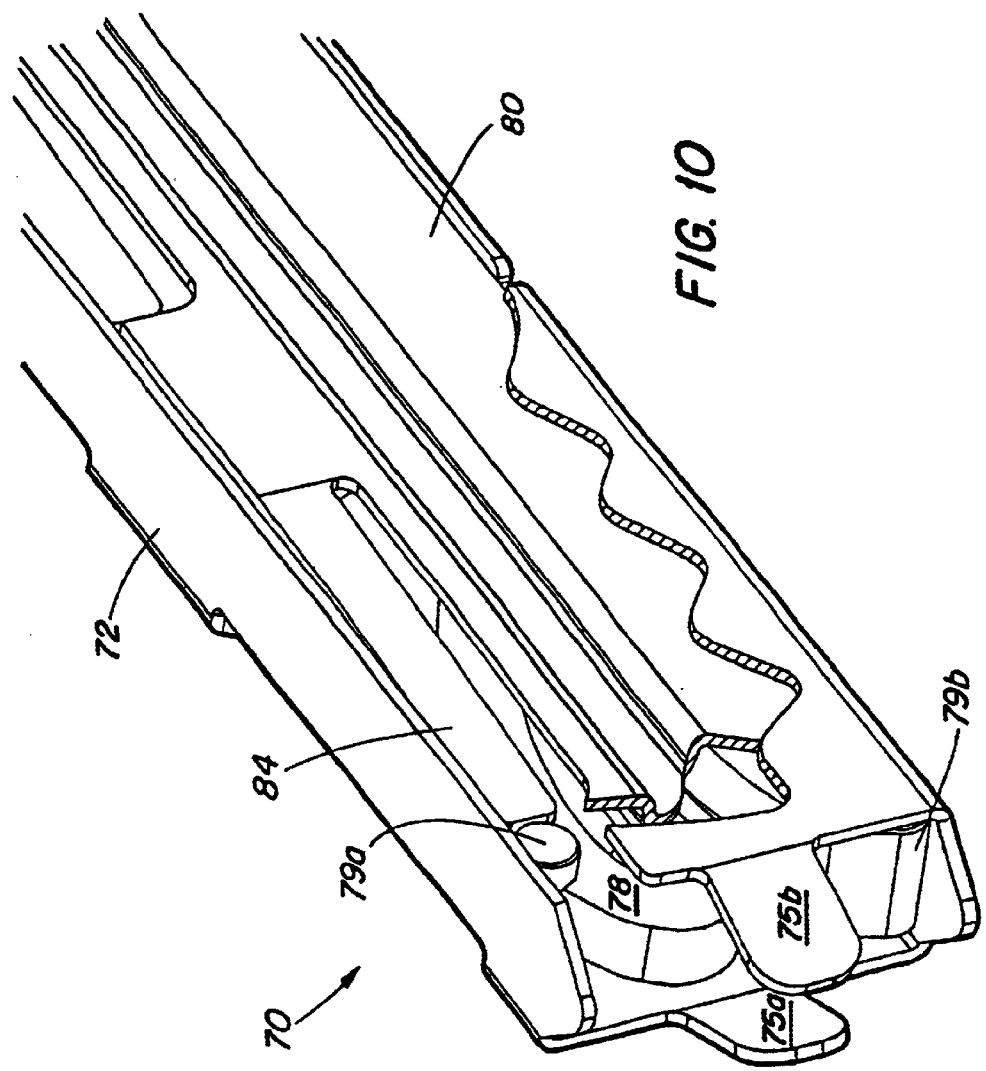

Referring generally to FIGS. 6–8, according to one embodiment of the invention, the first portion of the stroke of trigger 144 is a feed stroke that advances yoke 50 and feeder bar 80 relative to the fixed channel 72. When the feeder bar 80 is advanced, the tabs 84 engage the clips 78 in channel 72 and advance the clips 78 toward the distal end of applier 10. The most distal clip 78 is fed into the jaw assembly 90 (FIG. 1). FIGS. 8–10 are partial cut-away views of the clip feeder assembly 70 illustrating the advancement or indexing of clip 78 to the most distal position during the feed stroke. For clarity of illustration, the distal end of feed bar 80 has been cut-away in FIGS. 8–10. FIG. 8 illustrates the beginning of a feed stroke, in which the tab 84 of feeder bar 80 is brought into contact with a boss 79a of clip 78 disposed in channel 72. In FIG. 9, further actuation of trigger 144 (FIGS. 6 and 7) moves the feeder bar 80 in a distal direction, which advances clip 78 toward the distal end of channel 72. In FIG. 10, the feeder bar 80 has advanced clip 78 to the most distal position in channel 72. For clarity, FIGS. 8–10 illustrate the advance of a single clip 78 toward the distal end of applier 10, but it will be appreciated that the clip channel 72 may include a plurality (e.g., 2–100) of clips 78, each of which is advanced by a tab 84 of feeder bar 80. In one embodiment, channel 72 holds twenty (20) clips.

Figure 19:
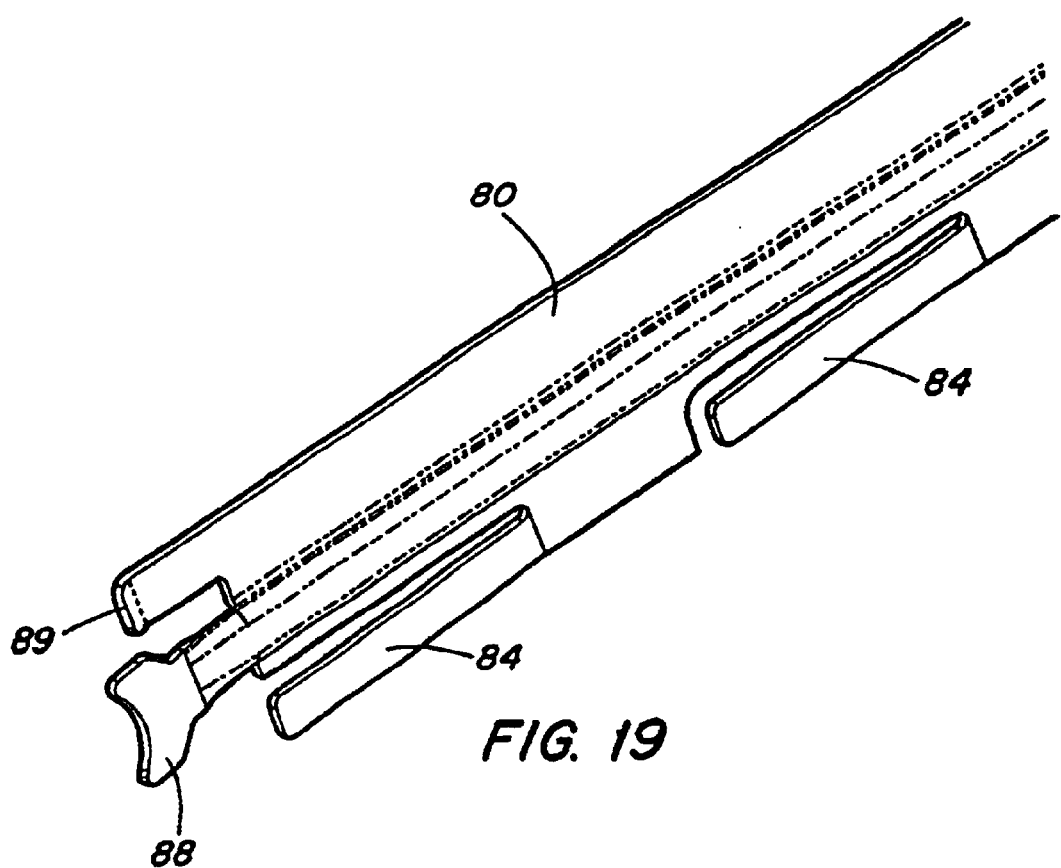
FIG. 19 is a perspective view of the distal end of a feeder bar in accordance with an embodiment of the subject matter disclosed herein.

During the feed stroke, the most distal clip 78 is fed from the channel 72 to the jaw assembly 90. In an exemplary embodiment, the distal end of channel 72 and feeder bar 80 include structural features adapted to feed the most distal clip into the jaw assembly 90. Referring to FIG. 19, the distal end of feeder bar 80 includes a feeder tab 88 adapted to contact the central, rear portion of the most distal clip 78 to push the clip 78 into the jaw assembly 90. In addition, feeder bar 80 includes a foot member 89 that rotates the rear of the most distal clip 78 during the return stroke so the rear portion of the clip 78 is positioned to contact feeder tab 88. The resulting alignment of the rear portion of clip 78 with feeder tab 88 is shown, for example, in FIG. 12. It will be noted, however, that FIG. 12 generally corresponds to the time at which clip 78 has been loaded into jaw assembly 90 and jaw assembly 90 and clip 78 have been opened wider (as described below) during the forward stroke. Thus, the rear portion of clip 78 is rotated by foot member 89 into alignment with feeder tab 88 during the return stroke that precedes the forward (clip feeding and clip opening) stroke. Preferably, the interior surfaces of the jaw assembly 90 that receive the clips 78 are of substantially the same width as the channel 72 to provide a smooth transition between the channel 72 and the jaw assembly 90.

Figure 20:
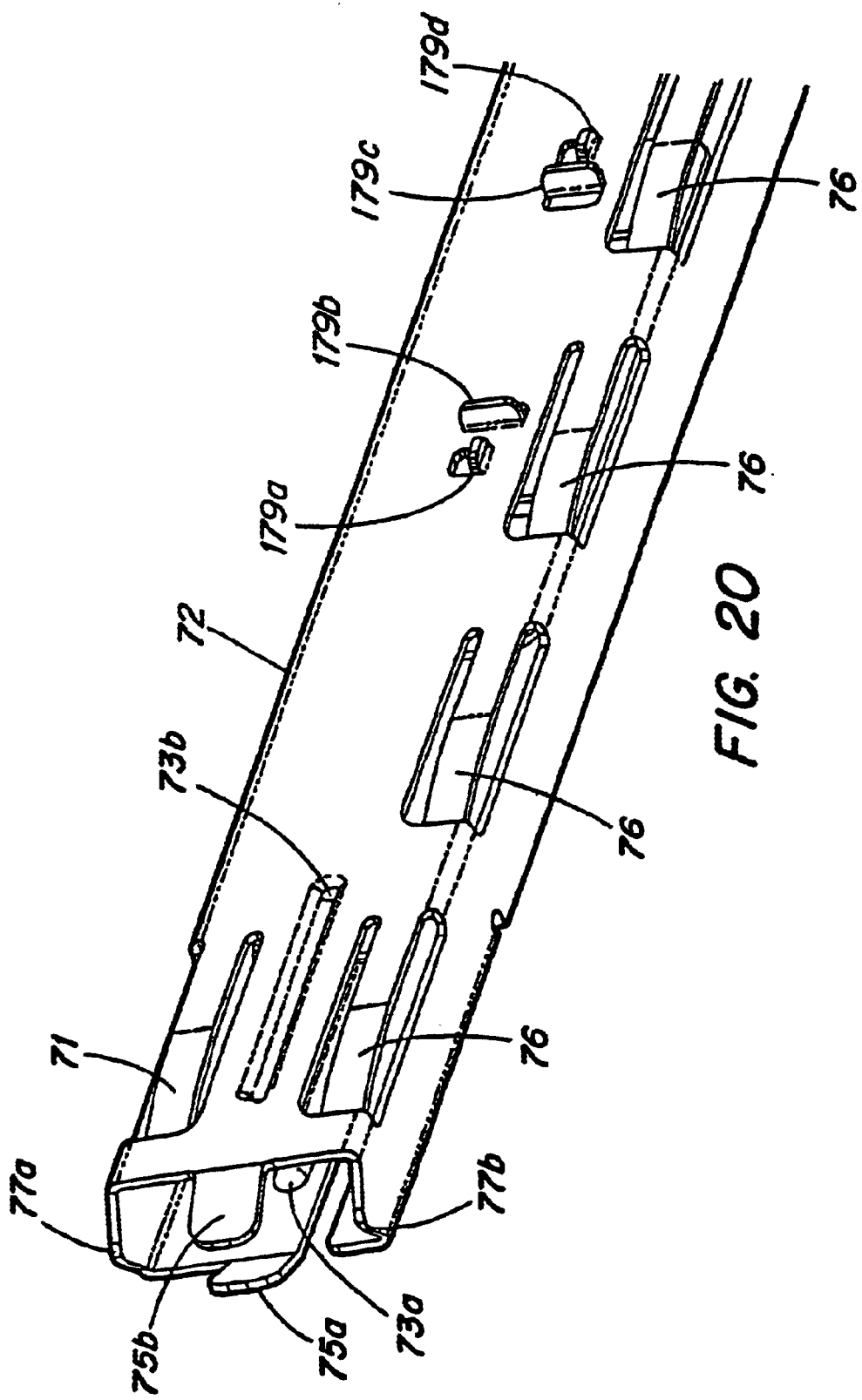
FIG. 20 is a perspective view of the distal end of a clip channel in accordance with an embodiment of the subject matter disclosed herein.

Referring to FIG. 20, the distal end of channel 72 includes a tab 71 that catches the boss 79b (shown, e.g., in FIGS. 8–10 and 12–14) on the most distal clip 78 when the foot member 89 (FIG. 19) of feeder bar 80 rotates the clip 78 during the return stroke, thereby limiting the rotation of the clip 78. In addition, opposing ribs 73a, 73b facilitate centering the rear of the most distal clip 78 (in the lateral direction) so the rear portion of the clip 78 is positioned to contact feeder tab 88 (FIG. 19). The distal end of channel 72 further includes upper and lower tabs 77a, 77b to provide a surface that facilitates the transfer of the clip 78 into the jaw assembly 90. In addition, opposing lateral tabs 75a, 75b serve to guide the clip 78 into the jaw assembly 90 and to inhibit lateral motion of the rear portion of the clip 78 when the clip 78 is in the jaw assembly 90. FIG. 20 also provides a view of tabs 76 that inhibit clips 78 from sliding in a proximal direction during the return stroke of feeder bar 80, and of tabs 179a–179d for securing a jaw member to clip channel 72.

Figure 12:
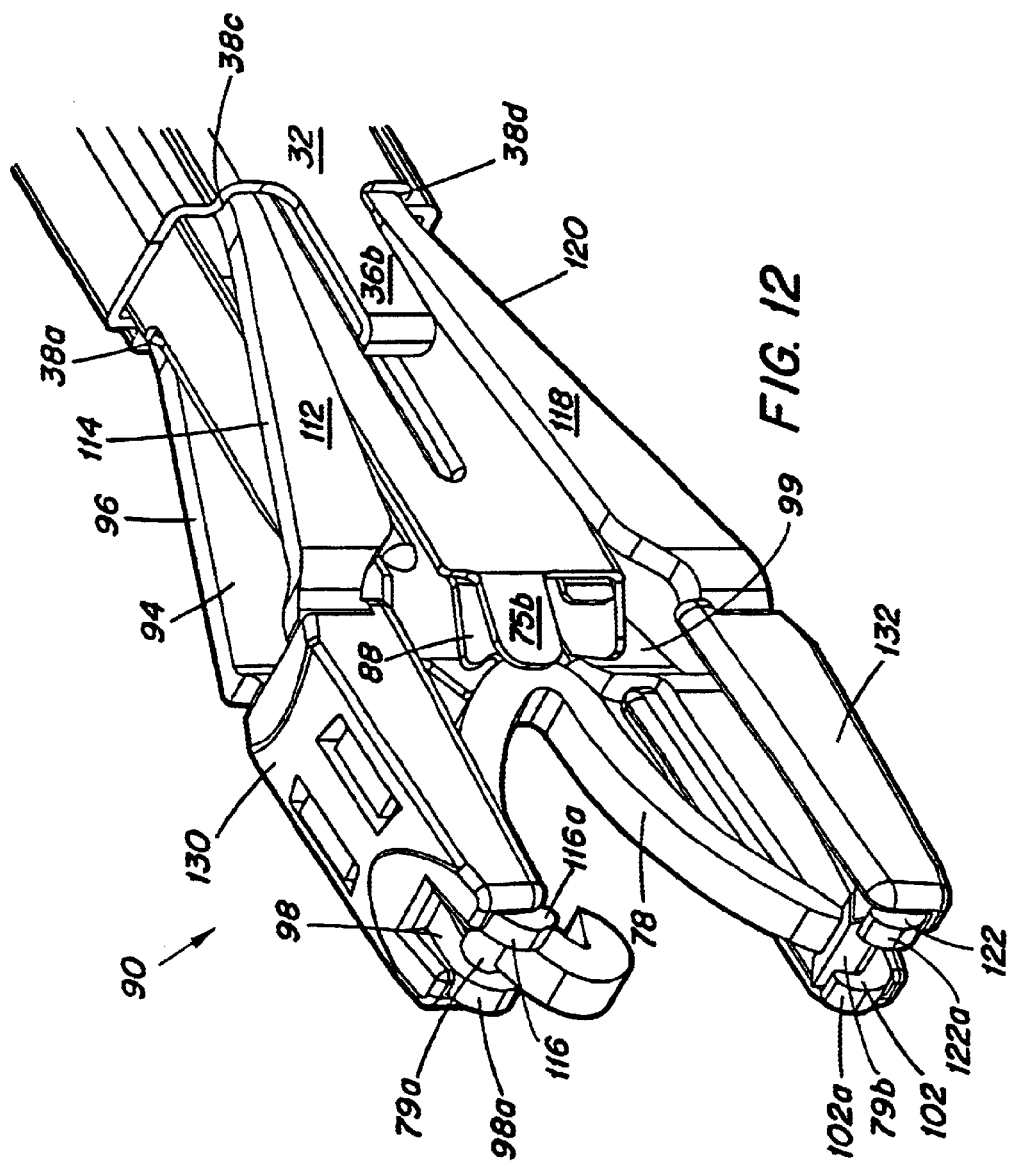
FIGS. 12–14 are perspective views of the jaw assembly during the process of closing a clip.

According to another aspect, the applier 10 is configured such that further actuation of the trigger 144 (FIGS. 6 and 7) functions to open a clip 78 disposed in the jaw assembly 90. The clips 78 are fed through channel 72 in a compressed configuration, which reduces the required diameter of the shaft assembly 22. The most distal clip 78 is fed into the jaw assembly 90 in the same compressed configuration. As illustrated in FIG. 12, first arm 98, second arm 102, third arm 116 and fourth arm 122 of respective first leg 94, second leg 99, third leg 112 and fourth leg 118 of jaw assembly 90 include respective catch structures such as first hook 98a, second hook 102a, third hook 116a and fourth hook 122a. Hooks 98a, 102a, 116a, 122a limit the forward motion of clip 78 in jaw assembly 90. Therefore, when further pressure is applied to the rear of clip 78 via the feeder tab 88 of feeder bar 80, the force is translated through the legs of clip 78, which causes the jaw assembly 90 (and the clip 78 contained therein) to open wider. The width to which the jaw assembly 90 may be limited by the cam surfaces 38a–38d of collar 32.

Figure 11:
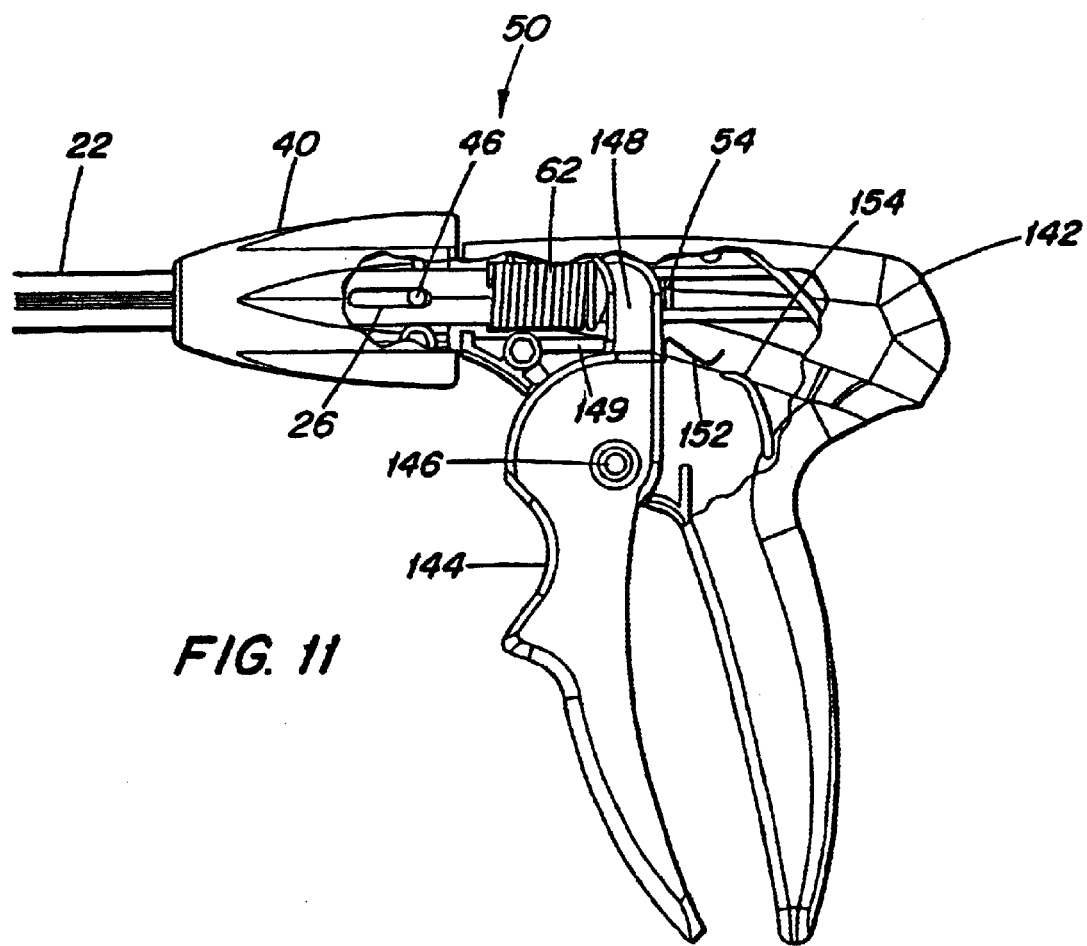
FIG. 11 is a partial cut-away view of a handle assembly in accordance with an embodiment of the subject matter disclosed herein.

Following completion of the feed stroke, further actuation of the trigger 144 actuates the jaw assembly 90. FIG. 11 is a side cut-away view of the proximal end of clip applier 10 with the device in a fully actuated state. Pin 46 is always in clearance with the channel 26 in shaft member 22. A rib 149 in handle body 142 limits the forward motion of the claw 148 portion of trigger 144, and hence limits the forward motion of yoke 50.

Figure 13:
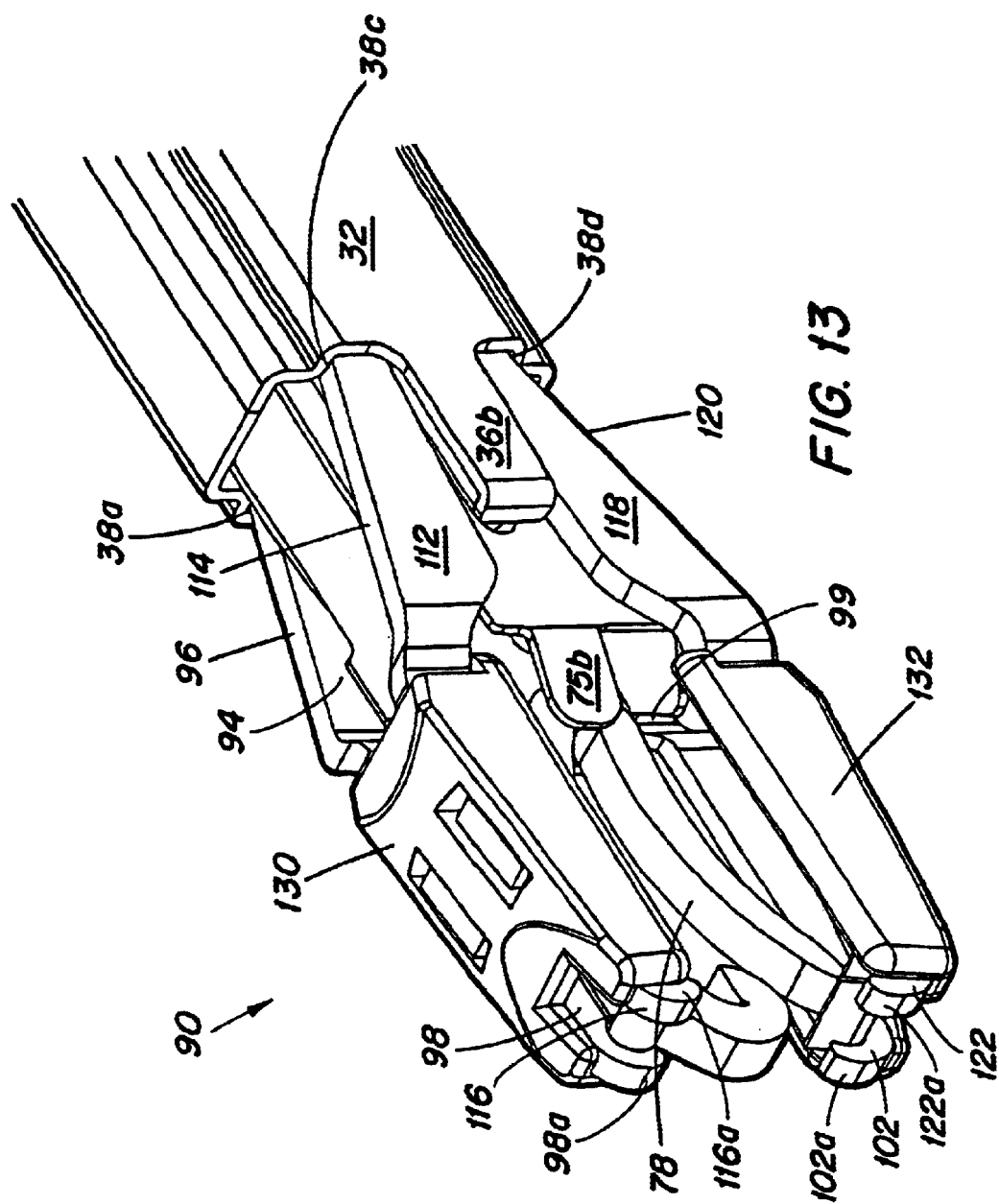
Figure 14:
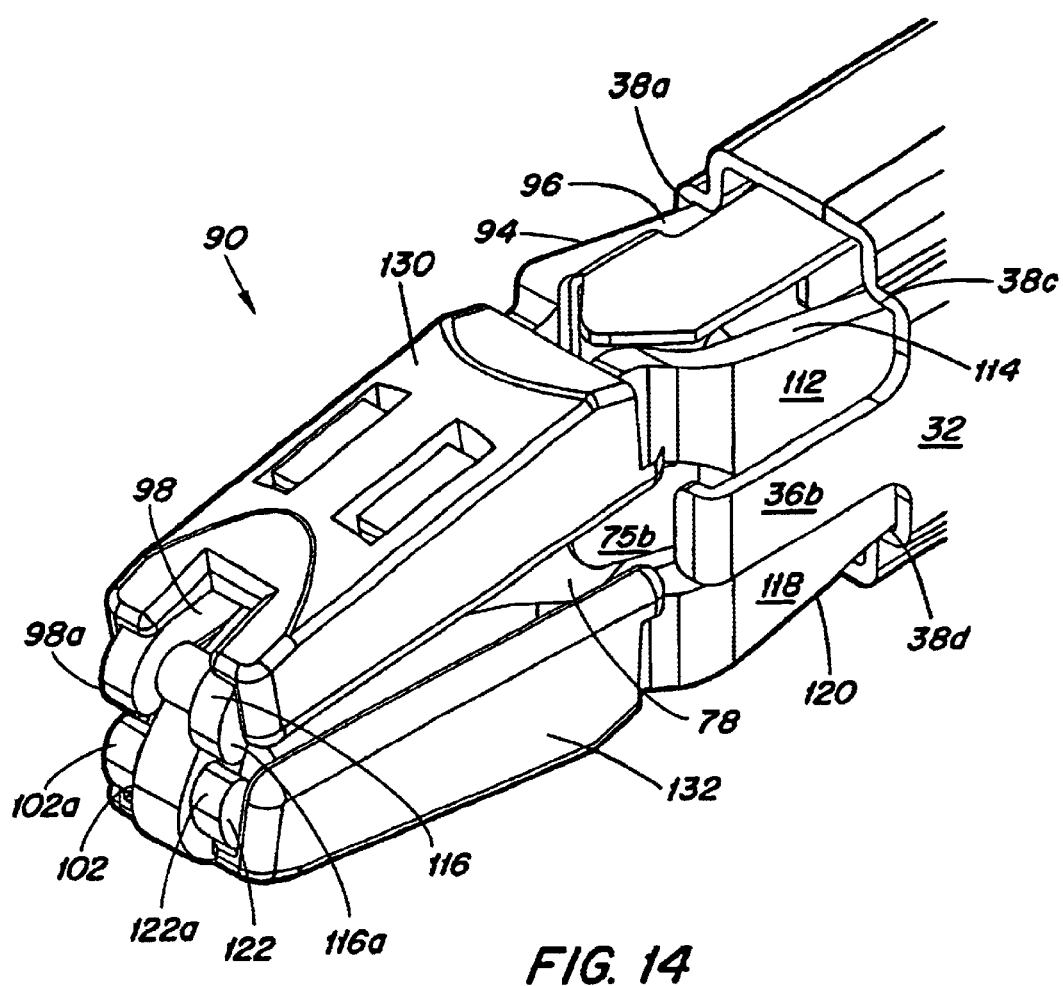

FIGS. 12–14 are perspective views of distal end of applier 10 illustrating the jaw assembly 90 while it is being closed. Referring first to FIG. 12, following completion of the feed portion of the stroke, a clip 78 is positioned in the jaw assembly 90, which is in an open configuration. According to another aspect, the second portion of the stroke of trigger 144 closes the jaw assembly 90. More particularly, referring to FIGS. 13–14, the second portion of the stroke moves outer shaft 22 in a distal direction relative to the fixed grip 142 (FIG. 1), knob 40 (FIG. 1), and clip channel 72 (FIGS. 2b and 2c). As the outer shaft 22 and collar 32 are moved in a distal direction, cam surfaces 38a–38d of collar 32 impinge on cam surfaces 96, 100, 114, 120, closing the jaw assembly 90. The use of four separate cams reduces the likelihood of scissoring as the jaw assembly 90 is closed.

While the jaw assembly 90 is closing, the feeder tab 88 (FIG. 12) of feed bar 80 remains in contact with the rear of clip 78. Closing the jaw assembly 90 tends to drive the rear of clip 78 in a proximal direction, which increases the pressure between the feeder tab 88 and the clip 78 in jaw assembly 90, thereby enhancing the stability of the clip 78 in the jaw assembly 90. This enhanced clip stability is particularly advantageous when a surgeon is pushing a clip 78 onto a vessel.

Additional features of applier 10 will be explained with reference to FIGS. 12–15. Each jaw arm 98, 102, 116, 122 terminates in a hook 98a, 102a, 116a, 122a, respectively. Hooks 98a and 116a of first jaw arm 98 and third jaw arm 116 cooperate to retain boss 79a of clip 78 in jaw assembly 90. Similarly, hooks 102a and 122a of second jaw arm 102 and fourth jaw arm 122 cooperate to retain boss 79b of clip 78 in jaw assembly 90. This configuration of jaw assembly 90 provides four distinct points of contact between jaw assembly 90 and clip 78, which reduces the likelihood of the jaw assembly 90 scissoring while it is closing. In addition, this configuration permits the force applied by the jaw assembly 90 to be applied to the distal end of the clip 78, which facilitates locking the clip 78. The rear (i.e., proximal) portion of clip 78 is retained between tabs 75a, 75b extending from the distal end of clip channel 72, which limits the range of lateral motion available to clip 78. In addition, the feed tab 88 (FIG. 12) of feed bar 80 prevents the rear (i.e., proximal) portion of clip 78 from being pushed back into the clip channel 72 when the clip 78 is being applied. Accordingly, the clip 78 is maintained stable in three dimensions while retained in the jaw assembly 90.

According to another feature, only a portion of the ratchet guide 154 (FIGS. 5 and 11) includes ratchet teeth. Preferably the length of ratchet guide 154 having teeth corresponds to the feed portion of the actuation stroke of trigger 144. Reversing the direction of feeder bar 80 during the feed stroke may cause the clip to become unstable, or even to fall out of the jaw assembly 90. The teeth on ratchet guide 154 inhibit feeder bar 80 from being moved in a proximal direction during the feed stroke. A second portion of ratchet guide 154, which preferably corresponds to the portion of the stroke during which the jaw assembly 90 is closed, permits the yoke 50 and the outer shaft 22 to move freely in the distal direction and the proximal direction. This allows a user to "approximate" a clip 78 during the closing process, i.e., to partially close a clip 78 then to re-open jaw assembly 90 to reposition a clip 78, if necessary.

In another aspect, the distal collar keys 36a, 36b provide a stop to prevent jaw assembly 90 from unintended closings during use, e.g., under compression as may be incurred during use in the body. Referring to FIG. 13, it can be seen that the distal portion of collar keys 36a, 36b include an inwardly-turned segment positioned to block the legs 112 and 118 from closing. However, the leg members 94, 99, 112, and 118 taper inwardly near the distal end of jaw assembly 90. Therefore, as illustrated in FIG. 14, when the shaft 22 is advanced, the keys 36a, 36b advance past the respective tapers in leg members 94, 99 and 112, 118, allowing jaw assembly 90 to close. Additionally, the collar keys 36a, 36b function as cams to facilitate re-opening jaw assembly 90 after the device is actuated and outer shaft 22 retracts.

FIG. 14 illustrates the jaw assembly 90 in a substantially closed configuration. Further actuation of the jaw assembly 90 will lock the clip 78. The distal motion of outer shaft 22 compresses the knob spring 64 (FIGS. 2b and 2c) between the flange 24a, 24b (FIGS. 2b and 2c) and the interior distal edge of knob 40 (FIGS. 2b and 2c), which provides the bias force to return trigger 144 and outer shaft 22 to their unactuated states (FIG. 6). After the jaw assembly 90 is closed, the user may release the trigger 144, and the bias force provided by knob spring 64 urges shaft 22 and feeder bar 80 in a proximal direction. This "resets" the applier 10 back to an unactuated state so that another clip may be fed to the jaw assembly 90.

During the reset sequence, the tabs 76 (FIG. 20) on clip channel 72 inhibit the clips 78 in channel 72 from moving in the proximal direction. The tabs 84 (FIG. 19) on the feeder bar 80 move across the clips 78 in channel 72 and snap into position behind the bosses of the clips 78. As the feeder bar 80 moves proximally, the foot member 89 of the feeder bar 80 contacts the boss 79b (FIG. 12) of the most distal clip 78 in the clip channel 72, causing the clip 78 to rotate. Rotation of the most distal clip 78 stops when the boss 79a (FIG. 12) contacts the most distal tab 71 (FIG. 20) of clip channel 72, which preferably positions the rear of clip 78 substantially in the center of the channel 72. As the feeder bar 80 continues to move proximally, the feed tab 88 is positioned adjacent the rear of the most distal clip 78, ready for the next actuation cycle.

Figure 15A:
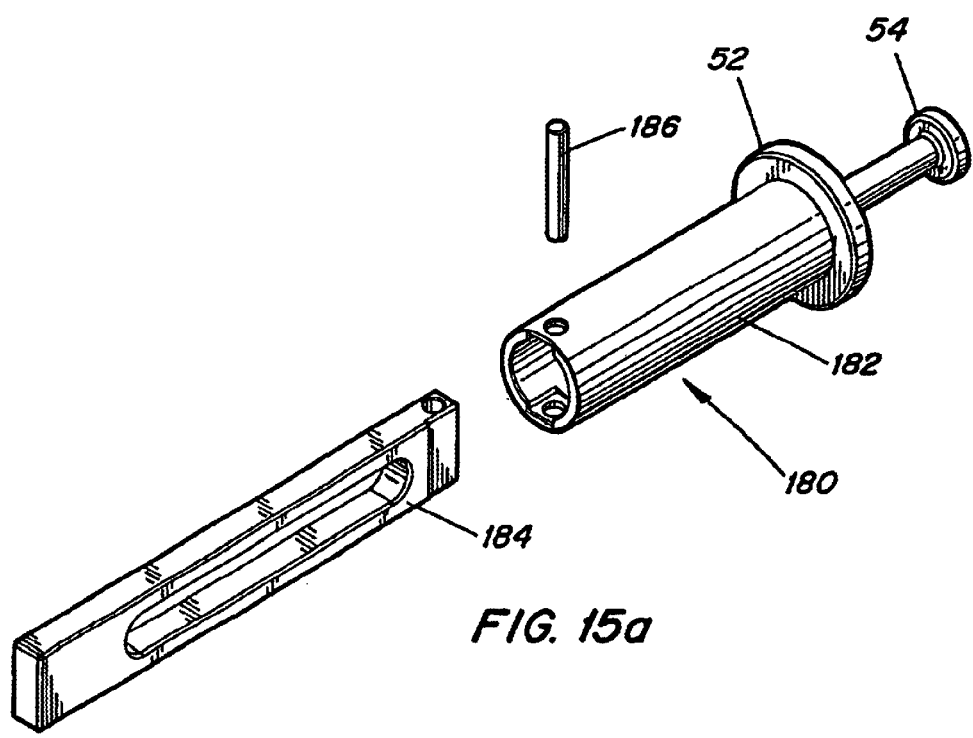
FIGS. 15a–15c are a perspective views of alternate embodiments of yokes in accordance with the subject matter disclosed herein.
Figures 15B, 15C:
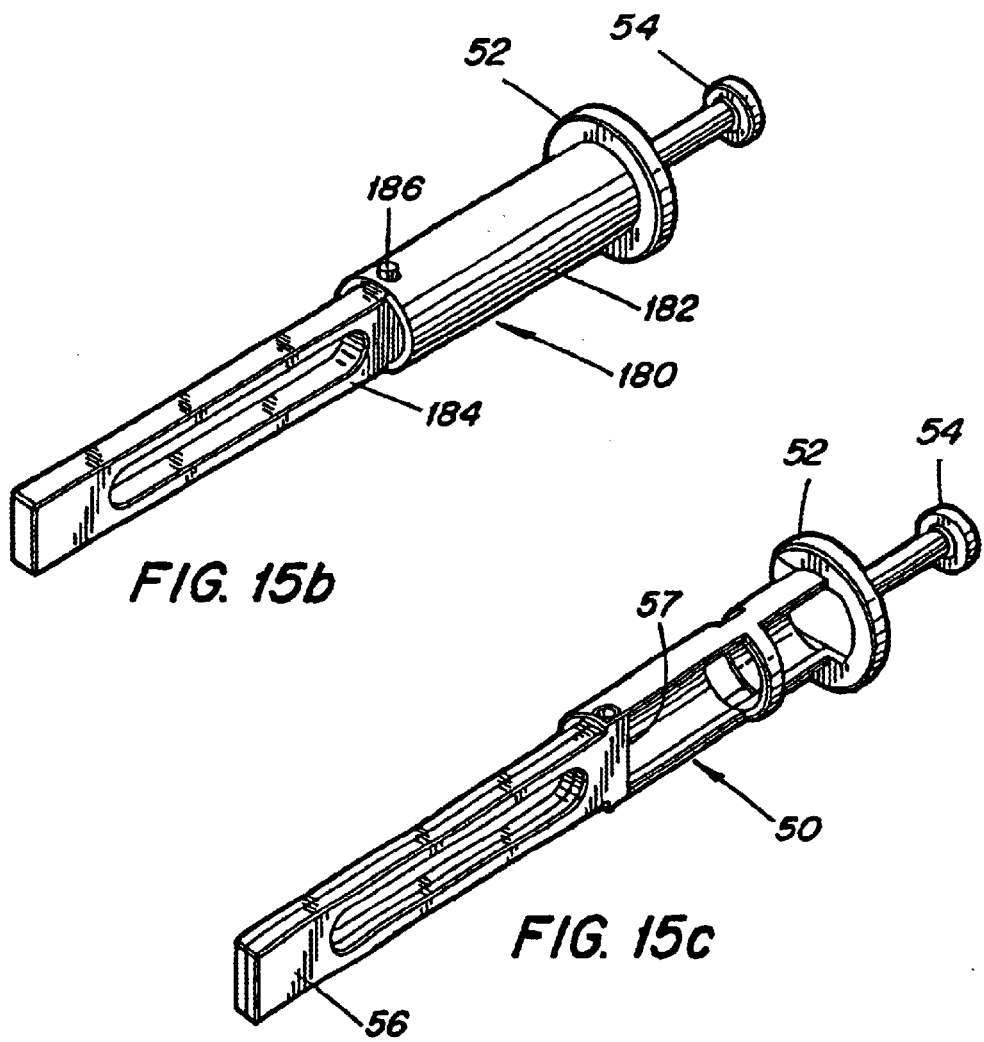

FIGS. 15a–15b illustrate alternate embodiments of a yoke in accordance with the subject matter disclosed herein. FIG. 15a is a perspective view of an alternate embodiment of a two-part yoke, generally designated 180, prior to assembly, and FIG. 15b is a perspective view of yoke 180 after assembly. Yoke 180 includes a first body portion 182 and a second body portion 184 connected by a pin 186. The feeder spring 60 (FIG. 6) may be disposed entirely within the first body portion 182 of yoke 180. In other respects, yoke 180 is substantially similar to yoke 50. Advantages of a two-piece yoke 180 as depicted in FIGS. 15a–15b include better retention of feeder spring 60 within the body of the yoke 180 and ease of assembly. FIG. 15c is a perspective view of yoke 50 depicted in FIG. 2, but from the opposite side to illustrate the interior distal edge 57 that receives the tab 86 (FIGS. 2b and 2c) of feeder bar 80.

Figure 16:
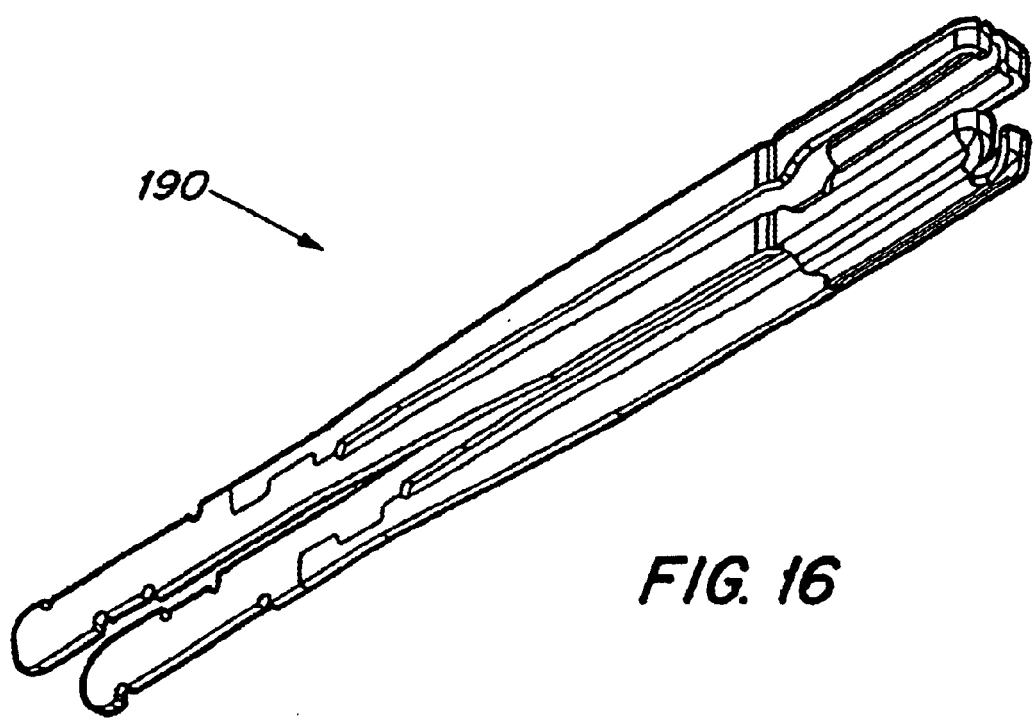
FIGS. 16–17 are perspective views of jaw assemblies in accordance with the subject matter disclosed herein.
Figure 17:
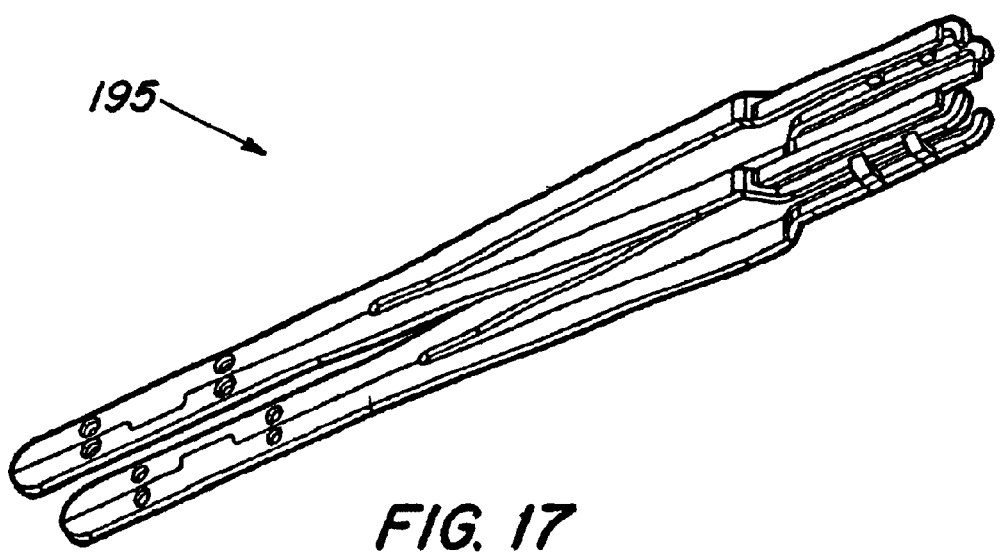

FIGS. 16–17 are perspective views of alternate embodiments of jaw assemblies, generally designated 190 and 195, respectively, in accordance with the subject matter disclosed herein. The jaw assemblies 190 and 195 depicted in FIGS. 16–17 are substantially similar to jaw assembly 90, but are particularly advantageous when used with an applier 10 having a shaft assembly 20 with a smaller diameter, e.g., 5 millimeters. The principal distinction between the jaw assemblies 190 and 195 depicted in FIGS. 16–17 and jaw assembly 90 is the elimination of bridge members 104, 124 (FIG. 2c) in favor of making each jaw member a discrete component.

Figure 21:
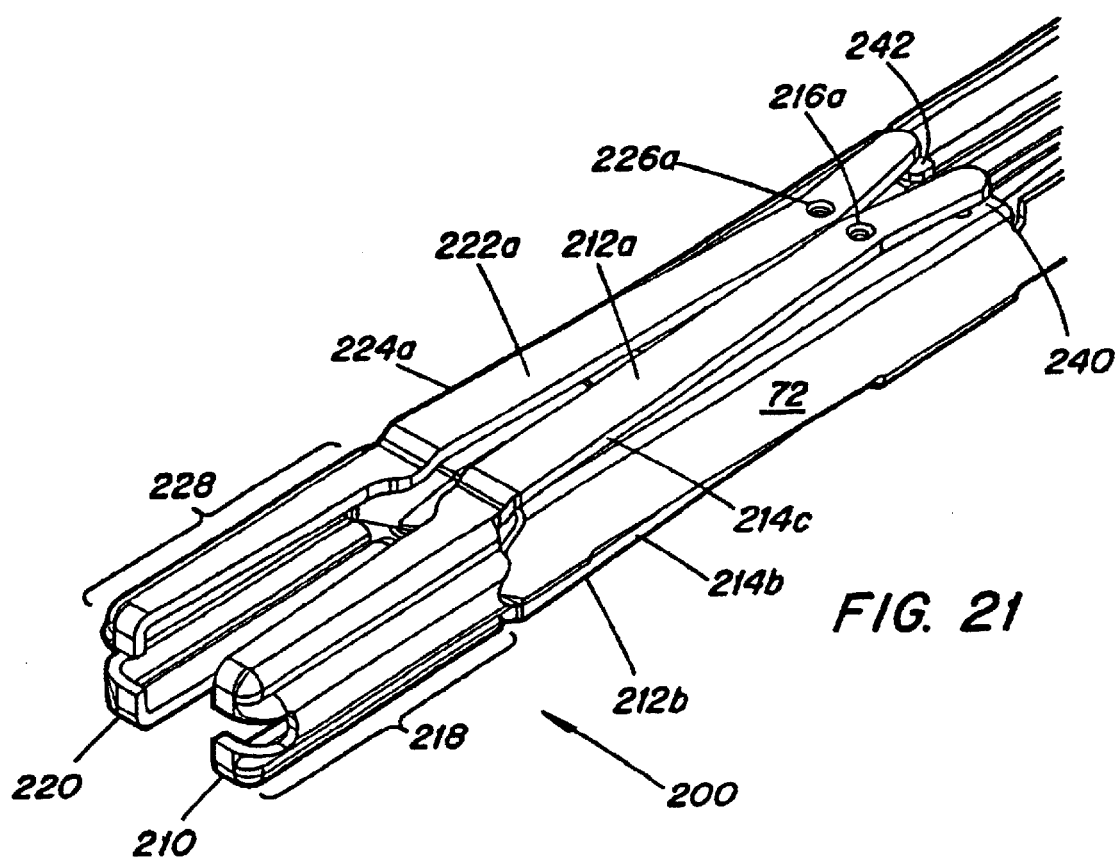
FIGS. 21–24 are perspective views of an alternate embodiment of a jaw assembly in accordance with the subject matter disclosed herein.

FIGS. 21–24 are perspective views of the distal end of a clip applier 10 illustrating an alternate embodiment of a jaw assembly, generally designated 200. FIG. 21 illustrates the distal end of the applier 10 with the collar 32 removed to better illustrate the jaw assembly 200. The jaw assembly 200 includes a first jaw member 210 including leg member 212a connected to the clip channel 72 at a pivot point 216a, and leg member 212b connected to the clip channel 72 at a pivot point (not visible) on the opposite side of clip channel 72. Each leg member 212a, 212b has a respective cam surface 214a, 214b. The distal end of the jaw assembly 200 forms a first jaw 218. The second jaw member 220 may be substantially identical to the first jaw member 210. Second jaw member 220 includes leg member 222a connected to the clip channel 72 at a pivot point 226a, and leg member 222b (FIG. 23) connected to clip channel 72 at a pivot point (not visible) on the opposite side of clip channel 72. Leg member 222a has a cam surface 224a, and leg member 222b (FIG. 23) has a similar cam surface (not visible). The distal end of the jaw assembly 200 forms a second jaw 228. Tabs 240, 242 extend from the surface of clip cartridge 72 and function as cams to bias the proximal ends of jaw legs 212a and 222a, respectively, outwardly. Likewise, a corresponding pair of tabs (not visible) extending from the opposite surface of clip cartridge 72 can be provided as cams to bias the proximal ends of jaw legs 212b and 222b outwardly. This tends to bias the jaw assembly 200 toward a closed configuration.

Figure 22:
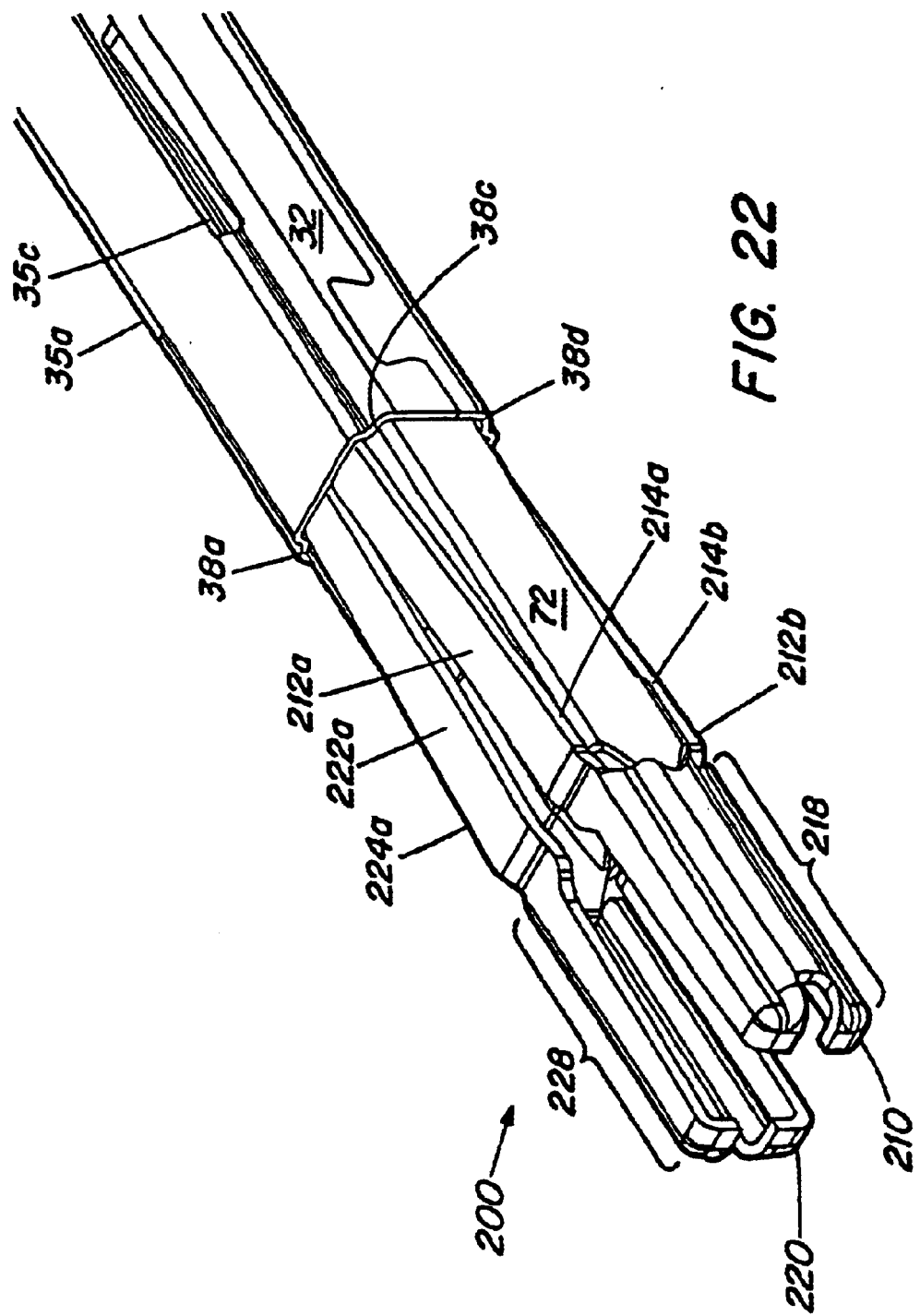
Figure 23:
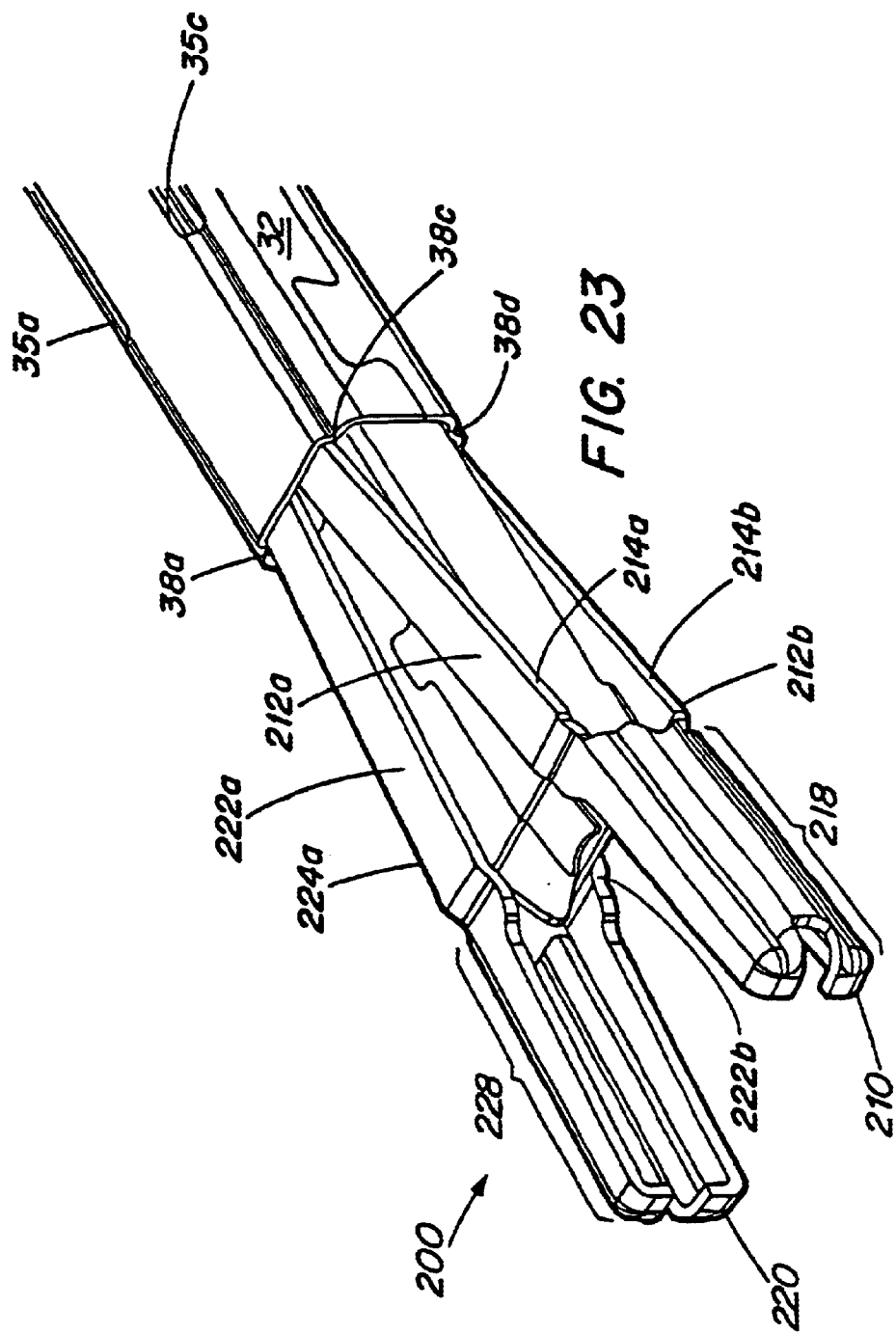
Figure 24:
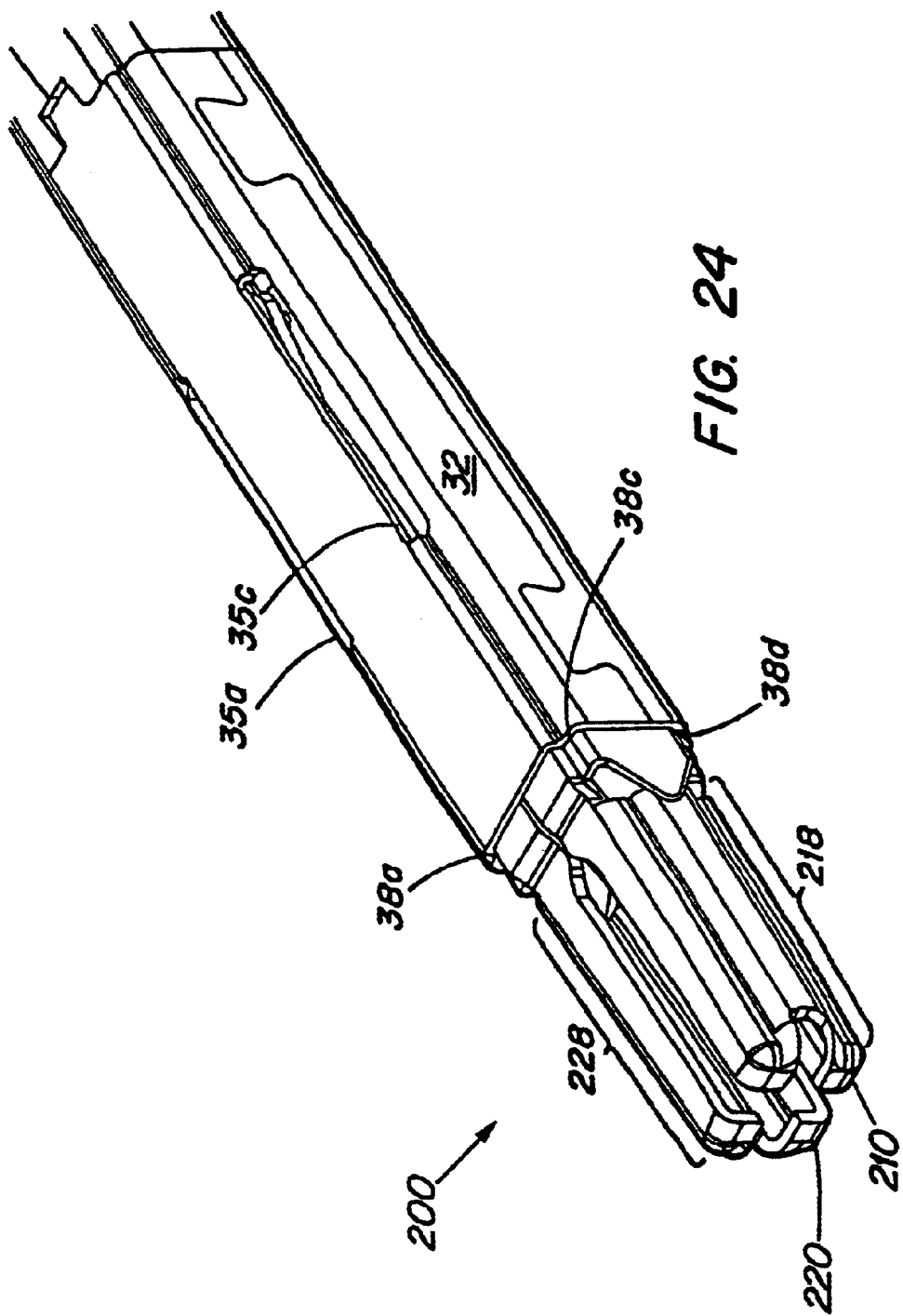

It will be appreciated that jaws 218, 228 may be opened and closed by pivoting the jaw members 210,220 about their respective pivot points (e.g., pivot points 216a, 226a, and the opposing pivot points not shown). FIGS. 22–24 are sequence views of the distal end of the applier 10 that illustrate closing the jaw assembly 200. FIG. 22 depicts the jaw assembly 200 in the clip feed position, in which the jaws 218, 228 preferably are substantially aligned with surfaces of the clip channel 72 to facilitate the smooth transfer of a clip 78 from the clip channel 72 into the jaw assembly 200. As described above, tabs (e.g., tabs 240, 242 shown in FIG. 21 and the opposing tabs not shown) of clip channel 72 bias the proximal ends of jaw legs 212a, 212b, 222a, 222b, respectively outwardly. Collar 32 limits the outward motion of the proximal ends of jaw legs 212a, 212b, 222a, 222b, respectively, which preferably are dimensioned such that the jaw assembly 200 is at rest as depicted in FIG. 22.

FIG. 23 depicts the jaw assembly 200 in an open configuration. As discussed above, driving a clip 78 in the jaw assembly 200 forward will open the jaw assembly 200 (the clip 78 is omitted in FIG. 23 for clarity of illustration). The opening of the jaw assembly 200 is limited by contact between the cam surfaces 214a, 214b, 224a (as well as the cam surface for leg member 222b, not visible) of the jaw members 210 and 220 and the corresponding cam surfaces 38a–38d of the collar 32.

FIG. 24 depicts the jaw assembly 200 in a closed configuration. As described above in connection with FIGS. 12–14, when collar 32 is advanced, cams 38a–38d impinge on the cam surfaces 214a, 214b, 224a (as well as the cam surface of leg member 222b, not visible), which closes the jaw assembly 200. Collar 32 includes slots (e.g., slots 35a and 35c and opposing slots not visible) that allow the respective rear portions of jaw legs 212a, 212b, 222a, 222b to extend outwardly so that the jaws 218, 228 can close.

Figure 25:
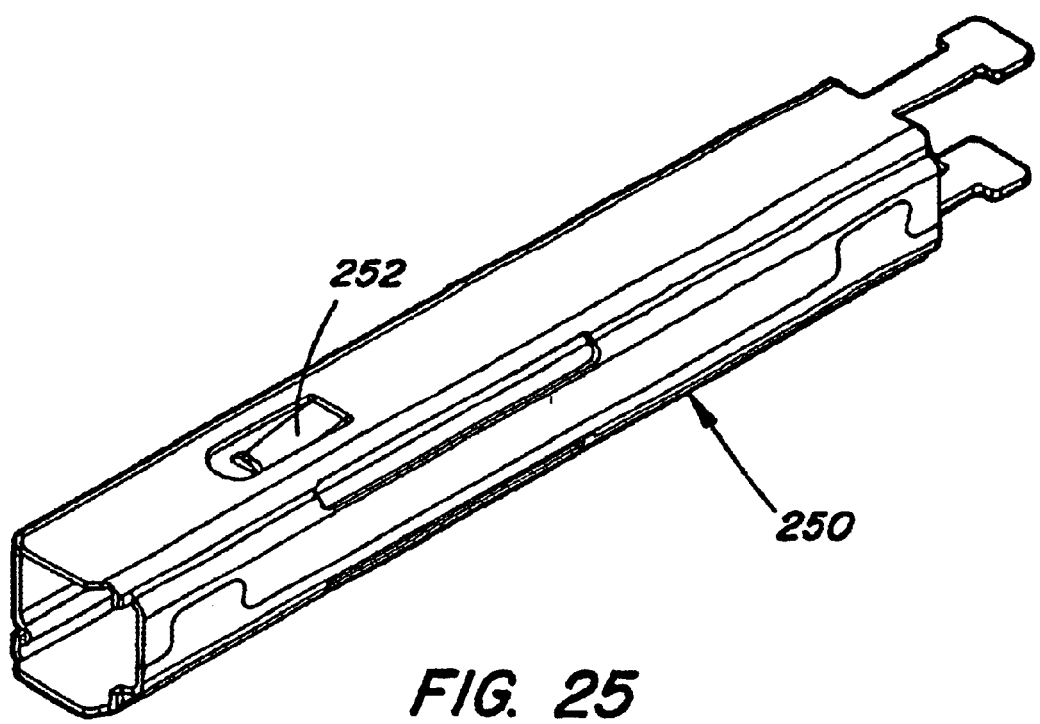
FIG. 25 is a perspective view of an alternate embodiment of a collar in accordance with the subject matter disclosed herein.

FIG. 25 depicts an alternate embodiment of a collar 250 adapted for use with the jaw assembly 200 depicted in FIGS. 21–24. Collar 250 is substantially similar to the collar 32 depicted in FIGS. 21–24, and includes a tab 252 that extends into the chamber defined by the collar 250 to prevent jaw members 210, 220 from unintended closing, e.g., due to pressure inside the body cavity. When the jaw assembly 200 is in the unactuated position or the partially-actuated position, tab 252 fits between leg members 212a, 222a to prevent jaw assembly 200 from closing. By contrast, when jaw assembly 200 is fully actuated, the tab 252 moves distally, allowing the jaw assembly 200 to close.

An exemplary embodiment of the invention has been described in which the clip cartridge 72 is retained substantially in a fixed spatial relationship with the fixed grip 142, and the actuation assembly moves the feeder bar 80 to advance clips 78 in the clip channel 72 and outer shaft assembly 20 to close the jaw assembly 90. One of ordinary skill in the art will recognize that the shaft assembly 20 could remain fixed, and the actuation assembly could move the clip channel 72 relative to the fixed shaft 22 to close the jaw assembly 90. For example, the clip channel 72 could be biased in a distal direction and the pivot point 146 of trigger 144 could be repositioned such that actuating the trigger 144 retracts clip channel 72 in a proximal direction. Similarly, feeder bar 80 could be fixed, such that retracting clip channel 72 in a proximal direction advances clips 78 in the clip channel 72.

The structure of the clip applier 10 has been generally described in relation to a single embodiment. Alternate embodiments of some components have also been described. It will be appreciated that the alternate embodiments of the components do not substantially alter the steps involved in the operation of the clip applier 10. In light of this disclosure, modifications to the present invention will be apparent to one skilled in the art. The modifications are intended to fall within the scope of the claims that follow.

What is claimed is:

1. An apparatus for applying polymeric latching clips in an endoscopic surgical procedure, comprising:
   (a) an elongate assembly for containing polymeric latching clips and comprising a distal end;
   (b) a jaw assembly for receiving a clip from the elongate assembly, the jaw assembly comprising first, second, third and fourth jaw legs spaced apart from each other for substantially simultaneously engaging at least four portions of the clip, each leg extending from the distal end and actuatable toward at least one other opposing leg for compressing the clip; and
   (c) wherein the elongate assembly comprises first, second, third, and fourth pivot points, and the first, second, third, and fourth legs are pivotably attached to the respective first, second, third, and fourth pivot points.

2. The apparatus according to claim 1 wherein the elongate assembly comprises a fixed member, and the first, second, third, and fourth pivot points are disposed on the fixed member.

3. The apparatus according to claim 2 wherein the non-actuatable member comprises a channel for containing the clips.

4. The apparatus according to claim 1 wherein the first, second, third, and fourth legs comprise respective first, second, third, and fourth jaw cam surfaces, and the elongate assembly comprises a jaw actuating member axially movable into contact with the first, second, third, and fourth jaw cam surfaces for actuating the jaw assembly; and wherein the jaw actuating member comprises first, second, third, and fourth distal cam surfaces respectively engageable with the first, second, third, and fourth jaw cam surfaces in response to movement of the jaw actuating member toward the jaw assembly.

5. The apparatus according to claim 4 wherein the jaw actuating member comprises a shaft, and the first, second, third, and fourth distal cam surfaces are formed on the shaft and generally spaced around a cross-section of the shaft.

6. An apparatus for applying polymeric latching clips in an endoscopic surgical procedure, comprising:
   (a) an elongate assembly for containing polymeric latching clips and comprising an axially movable distal end section, the distal end section comprising a plurality of distal cam surfaces generally spaced around a cross-section of the distal end section;
   (b) a jaw assembly comprising first and second opposing jaws for compressing a clip therebetween, the jaw assembly extending from the elongate assembly;
   (c) an actuator assembly communicating with the distal end section for actuating the distal cam surfaces into contact with the jaw assembly to cam the first and second jaws toward each other; and
   (d) wherein the elongate assembly comprises a shaft generally interposed between the distal end section and the actuator assembly, and the shaft is actuatable by the actuator assembly for moving the distal end section; and wherein the elongate assembly comprises a channel for containing the clips, the channel is disposed within the shaft, and the shaft and distal end section are movable relative to the channel.

7. An apparatus for applying polymeric latching clips in an endoscopic surgical procedure, comprising:
   (a) an elongate assembly for containing polymeric latching clips, the elongate assembly comprising a distal end, an axially movable clip feeding member, and an axially movable jaw actuating member;
   (b) a jaw assembly extending from the distal end and comprising first and second opposing jaws for compressing a clip therebetween;
   (c) an actuator assembly actuatable through a first stage and a subsequent second stage of a forward stroke, the actuator assembly coupled with the clip feeding member for moving the clip feeding member into contact with the clip to feed the clip into the jaw assembly during the first stage, and the actuator assembly communicating with the jaw actuating member for moving the jaw actuating member into contact with the jaw assembly to close the clip during the second stage, wherein the clip feeding member remains coupled with the actuator assembly for maintaining contact with the clip during the second stage; and
   (d) wherein the actuator assembly comprises a movable yoke having a proximal end and a distal end, and the clip feeding member is operatively connected with the yoke and is urged thereby toward the distal end of the actuator assembly, during the first and second stages; and wherein the actuator assembly comprises a spring contacting the clip feeding member for biasing the clip feeding member toward the distal end of the yoke.

8. An apparatus for applying polymeric latching clips in an endoscopic surgical procedure, comprising:
   (a) an elongate assembly for containing polymeric latching clips, the elongate assembly comprising a distal end, an axially movable clip feeding member, and an axially movable jaw actuating member,
   (b) a jaw assembly extending from the distal end and comprising first and second opposing jaws for compressing a clip therebetween;
   (c) an actuator assembly actuatable through a first stage and a subsequent second stage of a forward stroke, the actuator assembly coupled with the clip feeding member for moving the clip feeding member into contact with the clip to feed the clip into the jaw assembly during the first stage, and the actuator assembly communicating with the jaw actuating member for moving the jaw actuating member into contact with the jaw assembly to close the clip during the second stage, wherein the clip feeding member remains coupled with the actuator assembly for maintaining contact with the clip during the second stage; and
   (d) wherein the actuator assembly comprises a movable yoke, and the clip feeding member is operatively connected with the yoke and is urged thereby toward the distal end of the actuator assembly during the first and second stages; and wherein the jaw actuating member comprises a distal section for contacting the jaw assembly during the second stage, and an opposing proximal section, and the yoke is movable into contact with the proximal section for coupling the actuator assembly with the jaw actuating member during the second stage, and wherein the actuator assembly comprises a spring contacting the yoke for biasing the yoke toward the proximal section of the jaw actuating member.

9. An apparatus for applying polymeric latching clips in an endoscopic surgical procedure, comprising:
   (a) an elongate assembly for containing polymeric latching clips, the elongate assembly comprising a clip feeding member and a jaw actuating member;
   (b) a jaw assembly for receiving clips from the elongate assembly;
   (c) an actuator assembly comprising a ratchet surface, the actuator assembly coupled to the clip feeding member for moving the clip feeding member in a distal direction during a first stroke portion for feeding a clip into the jaw assembly, and forcing said clip to an open position once in the jaw assembly, and the actuator assembly communicating with the jaw actuating member for moving the jaw actuating member into engagement with the jaw assembly during a second stroke portion for closing the jaw assembly and allowing the jaw assembly to reopen;
   (d) a ratchet member coupled to the actuator assembly and actuatable into engagement with the ratchet surface during the first stroke portion for preventing movement of the clip feeding member in a proximal direction, and actuatable out of engagement with the ratchet surface during the second stroke portion for enabling movement of the jaw actuating member in both the distal and proximal directions; and
   (e) wherein the actuator assembly comprises a yoke which includes a spring which contacts the clip feeding member for moving the clip feeding member during the first stroke portion, and the yoke is movable into contact with the jaw actuating member for moving the jaw actuating member during the second stroke portion.

* * * * *